US011013534B2

(12) United States Patent
Boone, III

(10) Patent No.: US 11,013,534 B2
(45) Date of Patent: *May 25, 2021

(54) MICRODERMABRASION SYSTEM WITH ERGONOMIC HANDLE

(71) Applicant: Envy Medical, Inc., Westlake Village, CA (US)

(72) Inventor: N. Brendon Boone, III, Chatsworth, CA (US)

(73) Assignee: Envy Medical, Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/724,202

(22) Filed: Oct. 3, 2017

(65) Prior Publication Data

US 2019/0175222 A1 Jun. 13, 2019

Related U.S. Application Data

(63) Continuation of application No. 13/783,187, filed on Mar. 1, 2013, now Pat. No. 9,775,645.

(51) Int. Cl.
*A61B 17/54* (2006.01)
*A61B 17/00* (2006.01)
*A61B 17/32* (2006.01)

(52) U.S. Cl.
CPC ........... *A61B 17/545* (2013.01); *A61B 17/54* (2013.01); *A61B 2017/00424* (2013.01); *A61B 2017/00747* (2013.01); *A61B 2017/320012* (2013.01); *A61B 2217/005* (2013.01); *A61B 2217/007* (2013.01)

(58) Field of Classification Search
CPC ............... A61B 17/545; A61B 17/54; A61B 2017/00424; A61B 2217/007; A61B 2017/320012; A61B 2217/005; A61B 2017/00747

See application file for complete search history.

(56) References Cited

U.S. PATENT DOCUMENTS

| 6,250,996 | B1 | 6/2001 | Metcalf et al. |
| 6,322,568 | B1 | 11/2001 | Bernabei et al. |
| 8,147,489 | B2 | 4/2012 | Moses et al. |

(Continued)

FOREIGN PATENT DOCUMENTS

WO WO99/23951 5/1999

OTHER PUBLICATIONS

European Patent Office, Extended European Search Report, EP Application No. 14756617.8, dated Oct. 20, 2016, 7 pages.

(Continued)

*Primary Examiner* — Elizabeth Houston
*Assistant Examiner* — Michael G Mendoza
(74) *Attorney, Agent, or Firm* — Aka Chan LLP

(57) ABSTRACT

A microdermabrasion system includes an applicator tool including a central handle portion with a treatment tip at a distal end of the handle, where the treatment tip includes an abrading surface formed on a front surface of the tip. A proximal end of the elongated handle is coupled to first and second arms, forming an opening in the hand piece through which a user can insert one or more fingers. The handle supports a bottom side of a user's finger while the user grips the handle. In an implementation, the handle includes an indentation for at least one finger. In an implementation, the treatment tip is removable and replaceable.

36 Claims, 14 Drawing Sheets

(56) References Cited

U.S. PATENT DOCUMENTS

| | | |
|---|---|---|
| 8,236,008 B2 | 8/2012 | Boone et al. |
| 2002/0151908 A1 | 10/2002 | Mallett et al. |
| 2003/0208159 A1 | 11/2003 | Ignon et al. |
| 2007/0156124 A1 | 7/2007 | Ignon et al. |
| 2009/0125023 A1 | 5/2009 | Stephen et al. |
| 2010/0049177 A1 | 2/2010 | Boone, III et al. |
| 2011/0009882 A1 | 1/2011 | Remsburg et al. |
| 2011/0054490 A1 | 3/2011 | Hart |
| 2012/0136374 A1 | 5/2012 | Karasiuk |
| 2013/0345661 A1* | 12/2013 | Chang ............... A61B 17/3207 604/501 |

OTHER PUBLICATIONS

European Patent Office, Extended European Search Report, EP Application No. 20196329.5, dated Dec. 7, 2020, 9 pages.

* cited by examiner

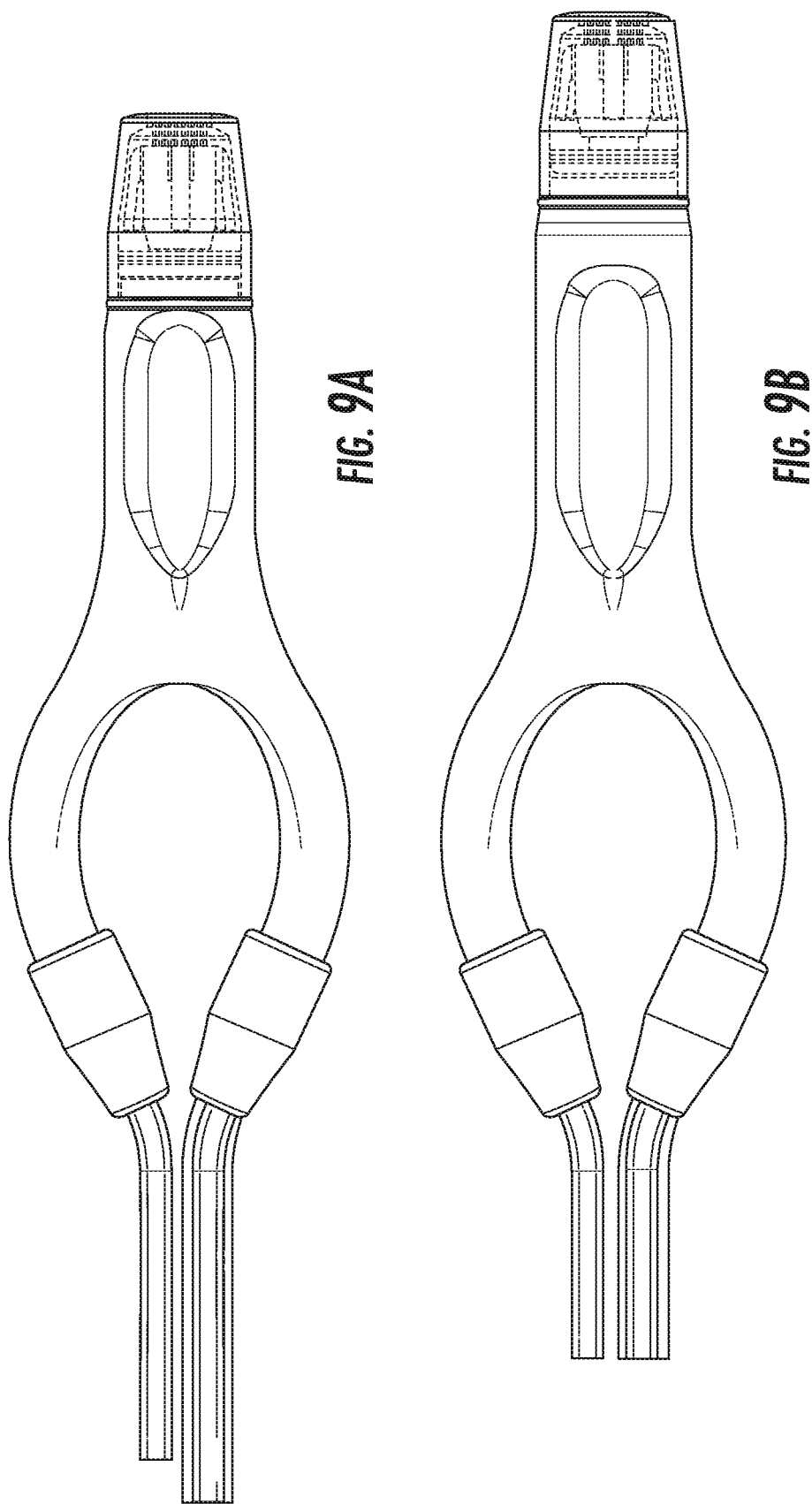

MICRODERMABRASION SYSTEM WITH ERGONOMIC HANDLE

CROSS-REFERENCE TO RELATED APPLICATIONS

This patent application is a continuation of U.S. patent application Ser. No. 13/783,187, filed Mar. 1, 2013, issued as U.S. Pat. No. 9,775,645 on Oct. 3, 2017, which is incorporated by reference along with all other references cited in this application.

BACKGROUND OF THE INVENTION

The invention relates to the field of devices to treat human skin and more specifically to a microdermabrasion tool.

As people age, they look for ways to maintain a youthful appearance. Some invasive cosmetic techniques include surgical approaches including eye lifts, face lifts, skin grafts, and breast lifts. However, these invasive techniques also have risks and potential complications. Some people have died during cosmetic surgery operations. Therefore, it is desirable to have noninvasive cosmetic techniques.

A noninvasive technique for obtaining a more youthful appearance is through microdermabrasion. Microdermabrasion is a process for removing dead cells from the outermost layer of the skin (the epidermis) to provide a younger and healthier looking appearance, remove wrinkles, clean out blocked pores, remove some types of undesirable skin conditions that can develop, and enhance skin tone.

The process of microdermabrasion must be performed with a certain degree of accuracy, so that underlying live layers of skin tissue are not removed or damaged, but that enough dead cells are removed to give effective results. There is a continuing demand for microdermabrasion systems that are easier, safer, and more comfortable to use. Therefore, there is a need for improved system, devices, and techniques for performing microdermabrasion.

BRIEF SUMMARY OF THE INVENTION

A microdermabrasion system includes an applicator tool including a central handle portion with a treatment tip at a distal end of the handle, where the treatment tip includes an abrading surface formed on a front surface of the tip. A proximal end of the elongated handle is coupled to first and second arms, forming an opening in the hand piece through which a user can insert one or more fingers. The handle supports a bottom side of a user's finger while the user grips the handle. In an implementation, the handle includes an indentation for at least one finger. In an implementation, the treatment tip is removable and replaceable.

A system for performing microdermabrasion is provided which includes an applicator tool having an abrasive tip with at least one opening therethrough, the tip being adapted to contact the skin of a patient; an abrasive member located internally of the applicator tool, and means for applying vacuum through the at least one opening, where upon application of vacuum a portion of the skin is drawn into contact with the abrasive member.

A wide variety of abrasive tips may be used with the system. This may include, for example, different types of abrasive elements such as bristles, meshes, abrasive particles, or combinations of these. Abrasive tipped devices or rotating brushes and cylinders coated with abrasive particles, can be used to remove skin layers. In a specific implementation an abrasive treatment tip is coated with diamond dust on a front surface. The tip can rotate. Many different sizes of tips are available. Thus, small skin surfaces such as the cheek, forehead, chin, and nose may be treated. Large surfaces such as the back, arms, or torso may also be treated.

In implementations, the treatment tip is designed to be removable and installable by the user. Further, the user can dispose of used or old tips or holders, or both, and easily replace them with new (or clean) ones. Also, the user can remove the tips to clean them or clean the passages to ensure the flow, vacuum and fluid, are clear, so that the microdermabrasion device will be operating at full efficiency. Also, in an embodiment, the tip and tip holder are designed to be low cost (e.g., made of less expensive materials) and disposable.

A microdermabrasion system includes an applicator tool (e.g., a hand piece) including a handle portion with a tip at a distal end of the handle, where the tip includes an abrading surface formed on a front surface of the tip, a proximal end of the handle, opposite the tip, where the proximal end is coupled to first and second arms. The arms form a gap, which includes a closed gap end and an open gap end. In a specific implementation, the first and second arms are positioned to curve around sides of at least one finger.

In an implementation, the handle includes an indentation (or a depression, notch, or groove) positioned on the handle to allow the index finger to rest in the indentation. The indentation can be a circular or oval shape to conform to the contours of the index finger. In other implementations, the indentation can include a textured pad to provide additional grip for the index finger. The handle can include one or more additional indentations for the thumb and middle finger to rest in.

A method of performing microabrasion is provided which includes: inserting at least one finger through a gap between two arms of a hand piece; applying a treatment tip to a skin surface; providing negative pressure through an opening in the treatment tip to establish a relative vacuum; drawing a portion of the skin surface through the opening and into contact with an abrasive member; and moving the treatment tip over the skin surface and microabrading the portion of the skin in contact with the abrasive member.

Microabraded skin particles are collected through a vacuum conduit through which the negative pressure is provided. Fluid may be applied to the skin though the opening in the treatment tip. In such instances, the vacuum conduit will also collect excess fluid.

The vacuum provided by the negative pressure surrounds a perimeter of the abrasive, moderately abrasive or non-abrasive channel seal member. In a microabrasion application, this makes it so that microabraded skin particles are collected downstream of the abrasive member and from all locations surrounding the abrasive member. In other applications (but also in microdermabrasion), such an arrangement assists in the ability to move the device in any direction over the skin. The symmetric nature of the configuration avoids such need as experienced with other implements that have a certain directionality requirement (i.e., they must "point" in their direction of travel). In a microdermabrasion application, the present device configuration provides for applying not only any abrasive compounds as may be desired directly and immediately at the spot of abrasion, but also (or alternatively) other solutions or compounds offering various benefit(s).

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIGS. 9A-9B show a comparison of specific implementations of a hand piece.

FIG. 11 shows a top view of a specific implementation of a hand piece.

DETAILED DESCRIPTION OF THE INVENTION

Figure 1:
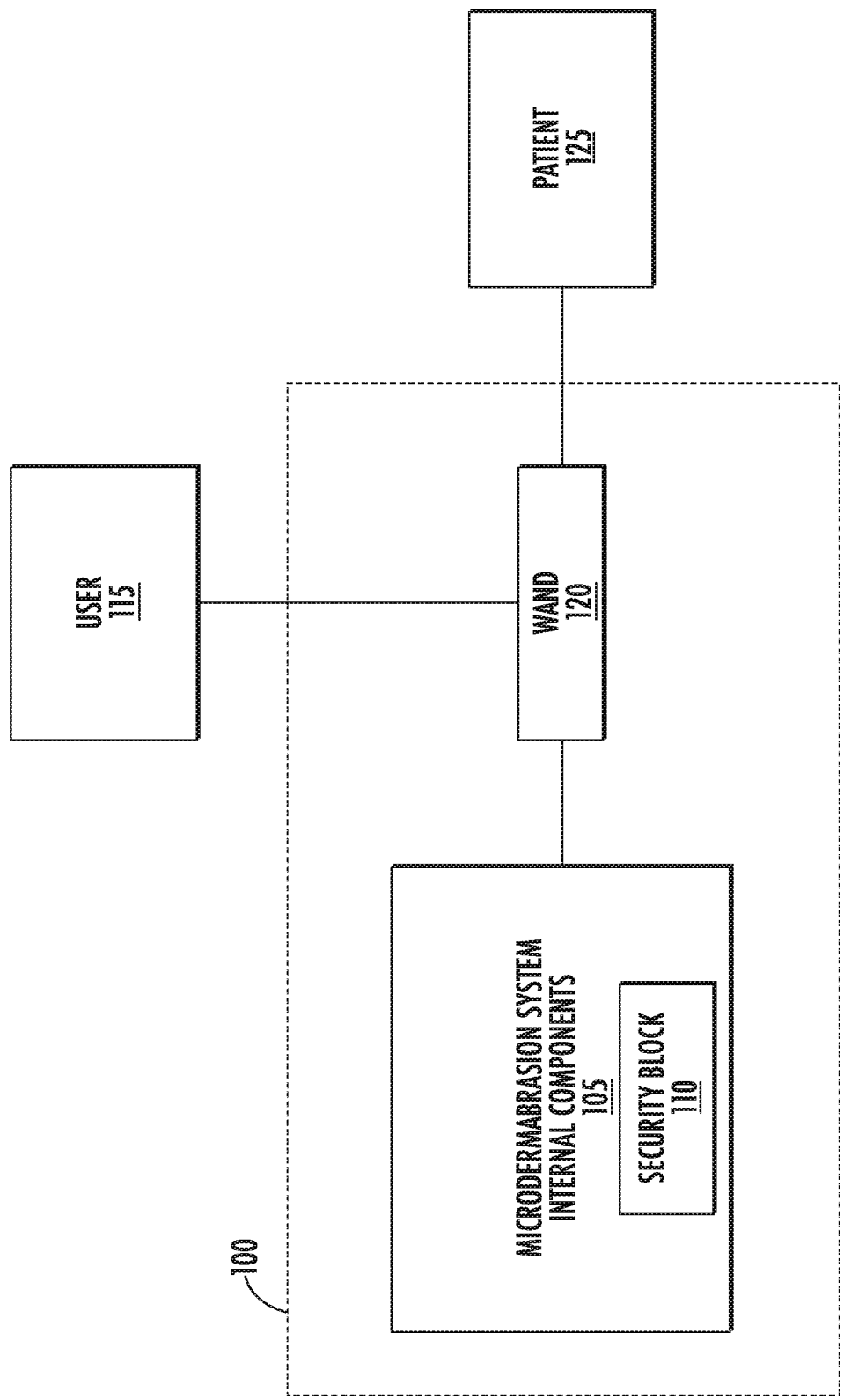
FIG. 1 shows block diagram of a microdermabrasion system.

FIG. 1 is a simplified block diagram of a microdermabrasion or dermabrasion system 100. The system has internal components 105 including a security block 110 that controls a security feature of the system. During a microdermabrasion treatment, a user 115 holds a hand piece or hand piece 120 and runs the hand piece over a patient's 125 skin to exfoliate it. The user may be a doctor, technician, operator, or aesthetician. After treatment, the patient leaves with a more youthful and healthful appearance.

Figure 2:
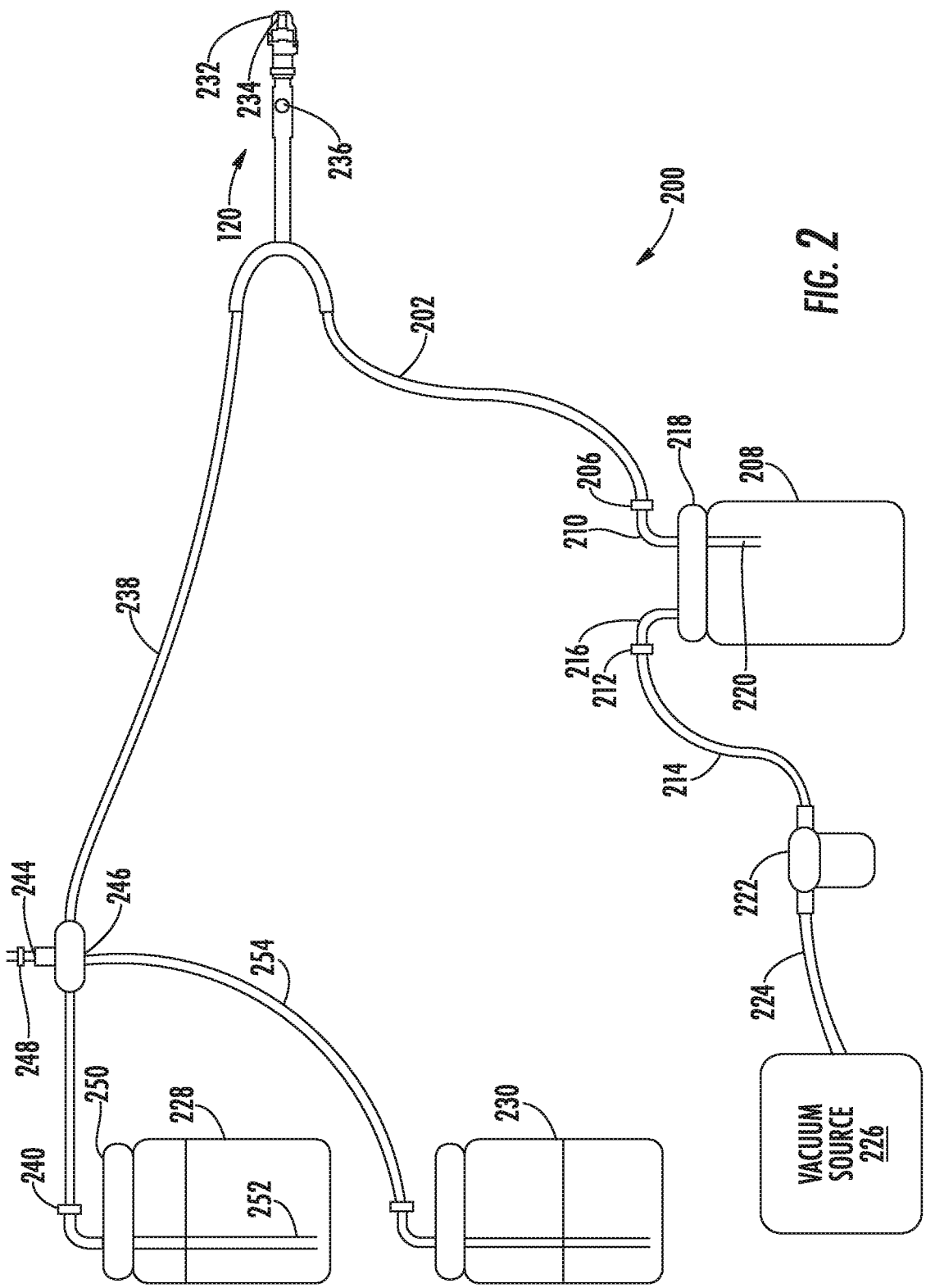
FIG. 2 shows an illustration of a microdermabrasion system.

FIG. 2 shows an overview of the flow of a microdermabrasion system 200. A vacuum line 202 is connected to a wand or hand piece 120. Vacuum line 202 connects to an input 206 to a collection reservoir 208 via an elbow 210, for example. An output 212 connects with a second vacuum line 214 via an elbow 216, for example. A manifold cover 218 seals the input (206, 210) and output (212, 216) connections with collection reservoir 208 which is typically a jar made of glass or plastic, for example. An extension tube 220 connects with inputs 210 and 206 and extends into the collection reservoir. The collection reservoir holds the waste materials (e.g., abraded skin particles and, optionally, fluids) from the microdermabrasion process.

Optionally, a filter 222 may be provided between second vacuum line 214 and a third vacuum line 224 which connects to a vacuum source 226. Filter 222 ensures that no fluid, skin particles, abrasive particles, or other materials collected by collection reservoir 208 are transported to vacuum source 226.

Any type of filter may be used. For example, in a specific embodiment, filter 222 is an in-line condensation or hydrophobic filter, such as a water condenser produced by Wilkerson Labs and available as part number F0001-000 from Nor-Cal Controls, Incorporated of San Jose, Calif.

Vacuum source 226 may be any type of vacuum source such as a vacuum pump, an ejector (e.g., single-stage ejector and multi-stage ejector), or a vacuum blower. In an implementation, the vacuum source creates negative pressure compared to the pressure at the hand piece tip, so that there is suction at the tip (i.e., there is a pressure difference between the pressure at the vacuum source and tip). Because of this suction or negative pressure, air, fluid, particles, and other matter at the tip are drawn to the vacuum source (through the collection reservoir). Further, in an implementation, the negative pressure also draws fluid out of a first fluid reservoir 228, a second fluid reservoir 230, or both to the tip, where is it pulled back into the collection reservoir. The suction is a fluid path that can conduct any fluid, including liquids or gases.

An example of a microdermabrasion device capable of delivering fluids to skin is the SilkPeel® Dermalinfusion® system by Envy Medical, Inc.™. Vacuum source 226 may generate a vacuum pressure from about −1 pound per square inch to about −14 pounds per square inch. For example, the vacuum pressure may be about −3, −4, −5, −6, −7, −8, −9, −10, −11, −12, −13, or more than −14 pounds per square inch. In some embodiments, the vacuum pressure may be less than 1 pound per square inch.

Vacuum source 226 may include a vacuum pressure adjustment control so that a user can vary the vacuum pressure. In a specific embodiment, the vacuum pressure adjustment control is a knob that can be rotated to change the vacuum pressure. In other embodiments, the vacuum pressure adjustment control is one or more push buttons, a slider bar, or other. A vacuum pressure gauge may indicate the current vacuum pressure. In a specific embodiment, the vacuum pressure gauge is a digital gauge. In another embodiment, the vacuum pressure gauge is a dial gauge. In yet another embodiment, the vacuum pressure adjustment may be a soft button displayed on a touch screen graphic user interface. Such user interface may be a panel embedded in the console of the device itself or an application running on a separate tablet computer and communicating with the microdermabrasion machine via a connection (e.g., USB, Bluetooth, or Wi-Fi interface). Likewise, the vacuum pressure gauge may be displayed on the same panel.

In a specific embodiment, vacuum source 226 includes a fluid flow adjustment control so that a user can vary the fluid flow settings. The fluid flow may range from about 0 milliliters per minute to about 140 milliliters per minute. For example, the fluid flow may be about 10, 20, 30, 40, 50, 60, 70, 80, 90, 100, 110, 120, 130 milliliters, or more than 140 milliliters per minute. In a specific embodiment, the fluid adjustment control is a knob that can be rotated to change the fluid flow. A fluid may be a liquid or gas. In other embodiments, the flow adjustment control is one or more push buttons, a slider bar, or other.

The flow control may be located in the console of the machine, the fluid delivery lines, or the handpiece itself. A fluid flow gauge may indicate the current flow rate. In a specific embodiment, the fluid flow gauge is a digital gauge. In another embodiment, the fluid flow gauge is a dial gauge. Flow rate may be measured as a function of millimeters per minute or as percentage of total flow rate capacity (0-100 percent). In another embodiment, the flow adjustment may be a soft button displayed on a touchscreen graphic user interface. Such user interface may be a panel embedded in the console of the device itself or an application running on a separate computer (e.g., laptop, desktop, or tablet computer) and communicating with the microdermabrasion machine via a connection (e.g., USB, Bluetooth, or Wi-Fi interface). Likewise, the flow rate gauge may be displayed on the same panel.

Hand piece 120 includes a tip holder 232 which holds a tip 234. A first fluid delivery line 238 extends from hand piece 120 and connects to an output 240 of first fluid reservoir 228 via an elbow 242, for example.

A breather line 244 may be connected in-line via a joint 246, for example, or other interconnection, and includes an adjustable valve 248 or other means for varying an amount of air that is allowed into first fluid delivery line 238. This feature allows, for example, the amount of vacuum pressure to be adjusted for a given fluid and allows fluids having different viscosities to be applied at the same vacuum pressure level, since different viscosities will require varying amounts of air to be introduced into breather line 244 to produce a constant vacuum pressure level.

Alternatively, a breather line or input with adjustment valve may be located on elbow 242 or directly on a manifold cover 250. Still further, a valve or other flow control mechanism 236 may be provided on hand piece 120 or in first fluid delivery line 238 to control the amount of fluid passing through the line. This feature can be provided alternatively, or in addition to breather line 248 discussed above.

The flow control mechanism or valve allows, for example, the user to turn off the flow of fluid to the hand piece so that the user can clean or replace the tip if it becomes clogged. The fluid flow control mechanism may be located on the hand piece as shown in FIG. 2 or anywhere along the fluid flow path such as on first fluid delivery line 238. Generally, however, the fluid flow control valve will be located on the hand piece or near the hand piece so that the user can quickly turn off the flow of fluid.

An input may be provided in manifold cover 250 which may be open to the atmosphere to prevent vacuum buildup in first fluid reservoir 228. Manifold cover 250 seals output (240, 242) connections with first fluid reservoir 228 which is typically a jar made of glass or plastic, for example, and contains lotions, vitamins, other skin treatment fluids, or combinations of these to be applied to the skin by hand piece 120. An extension tube 252 connects with output 240, 242 and extends into the first fluid reservoir to near the bottom of the first fluid reservoir to ensure that most all of the contents of the fluid reservoir are capable of being delivered through the system.

In a specific embodiment, second fluid reservoir 230 is also included. A second fluid delivery line 254 connects the second fluid reservoir to joint 246. Joint 246 may further include a valve to block or to permit the flow of fluid from the second fluid reservoir into first fluid delivery line 238.

The first fluid reservoir may include contents that are the same or different from the first fluid reservoir. For example, the first fluid reservoir may include topical anesthetics and the second fluid reservoir may include disinfectants. In various implementations, there are any numbers of fluid reservoirs. For example, an implementation may have more than two fluid reservoirs, such as three, four, five, six, seven, or more than seven fluid reservoirs. In such an embodiment, a valve coupled to a manifold would be used to select one or more of the solutions to enter main fluid delivery line.

Having more than one fluid reservoir allows, for example, different types of fluids to be used to treat different types of skin conditions that the patient may have without requiring the user to constantly remove the existing fluid reservoir and replace it with a new fluid reservoir that contains the appropriate fluid. For example, a patient with oily skin may require a different treatment regime than a patient with dry skin. The patient with the oily skin may thus be treated with fluid from the first fluid reservoir in which the fluid does not contain any oil-based products because such oil-based products may worsen the patient's skin condition. The patient with the dry skin may instead be treated with fluid from the second reservoir in which the fluid may include oil-based products to help moisturize the skin. In the case of multiple branched fluid delivery lines feeding a main fluid delivery line, the advantage therein would be to customize the mix of the fluids being delivered to the skin, wherein the patient may be treated with a specific mix of the various fluids simultaneously.

Abrasive particles, such as corundum crystals, sodium bicarbonate particles or other abrasive particles, including those discussed in U.S. Pat. No. 5,971,999 (which is incorporated by reference), for example may be included in the fluid reservoirs for delivery through the system to perform a microdermabrading function. However, in the system in this application, microdermabrasion is accomplished typically via a bristled tip, abrasive tip, or both. If used, the abrasive particles may be used together with any of the fluids mentioned above, with some other fluid carrier medium, such as those described in U.S. Pat. No. 5,971,999, for example, or both.

The fluid reservoirs may contain solution or a suspension for purposes other than abrasion or pure abrasiveness. The compositions used in the system can include a wide and diverse range of components. The *International Cosmetic Ingredient Dictionary and Handbook*, 15$^{th}$ edition, 2011, which is incorporated by reference, describes an extensive variety of cosmetic and pharmaceutical ingredients commonly used in the skin care industry, which are suitable for use in the compositions of the system.

General examples, types or categories, or both, of compounds that may be employed include: bleaching formulations (e.g., 2 percent to 4 percent hydroquinone, 2 percent kojic acid, 1 percent vitamin K, decapeptide-12 or other skin brightening peptides, and 1 percent hydrocortisone in an aqueous base); acne treatment formulations (e.g., salicylic acid, alcohol base buffered by witch hazel, bakuchiol and bisabolol, and others); fine lines/wrinkle treatment formulations (e.g., hyaluronic acid in an aqueous base); hydrating formulations (e.g., calendula, vitamins A, D, E, or other vitamins, or combinations of these in a mineral oil base); antioxidant formulations; free radical scavengers (e.g., vitamins A, E, K, or other vitamins, or combinations of these in a mineral oil base); pH adjusters; sunscreen agents; tanning agents and accelerators; nonsteroidal anti-inflammatory actives (NSAIDS); antimicrobial and antifungal agents; moisturizers; lightening agents; humectants; numbing agents; retinol (e.g., 0.2 percent to about 0.6 percent concentration); and water, or combinations of these.

The solution or suspension may contain extracts such as those from plants, vegetables, trees, herbs, flowers, nuts, fruits, animals, or other organisms, or combinations of these. Such extracts may be used to help condition the skin, provide a relaxing aroma, or both.

The solution or suspension may also contain viscosity increasing or decreasing agents, colorants, or combinations of these. In a specific implementation, the viscosity of the fluids used is about 1 centipoise (e.g., about 0.5 to 1.5 centipoise). However, in other implementations, the viscosity may range from 0.1 centipoise to 500 centipoise. The viscosity may be, for example, 0.2, 0.3, 0.4, 0.5, 0.6, 0.7, 0.8, 0.9, 1, 1.1, 1.2, 1.3, 1.4, 1.5, 1.6, 10, 20, 30, 40, 50, 60, 70, 80, 90, or more than 100 centipoise. In other applications the viscosity may be less than 0.1 centipoise.

In a specific implementation, the fluids, abrasive particles, or both for the fluid reservoirs may be packaged as a concentrated solution, powder, solids, or combinations of these to be mixed, diluted, or both by the microdermabrasion system, user, or both.

Other examples of product categories that may be employed alone or in combination with other compounds include, antiseptics, disinfectants, astringents, cleansers, pore decongestants, balms, botanicals, collagen stimulators, herbs, microemulsifiers, oxygen delivery vehicles, proteins, serums, skin firming agents, toners, topical anesthetics, emulsions, ointments, gels, tyrosinase inhibitors, and other related product categories.

Individually named products that may be used (with associated benefit indicated parenthetically) include: Aloe Vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); hydroquinones (bleaching); lactic acids (peel); magnesium ascorbic phosphate (free radical scavenger, collagen stimulator, bleaching); niacin (vascular dilation); phospholipids (moisturization); potassium (toning, psoriasis), and salicylic or glycolic acids (acne); and related products. Of course, any combination of such elements may be provided—even in connection with abrasive particles.

Any of the products listed may be used with the microdermabrasion treatment tips of the system. For example, the groves of a tip may be used to conduct botanicals, Aloe Vera, or alpha hydroxy, to name a few examples, to a patient's skin. The channels through which fluid is delivered may be partially formed in tip 234 and partially formed in tip holder 232. When tip 234 and tip holder 232 are put together, the grooves in each of these mate to form a complete channel opening.

As another example, coenzyme Q-10, lactic acids, or vitamin E, to name a few examples, may be conducted through an opening, surrounded by bristles, to the skin of a patient. The opening may extend to a position closer to patient's skin through a cylindrical column, nipple, or other structure to achieve a similar purpose.

Note, however, the present system may be used by eliminating the fluid reservoirs altogether, where microdermabrasion is performed in a "dry state" and first fluid delivery line 238 is simply left open to atmosphere, with or without a filter or valve, or both, for adjusting the amount or flow rate of air that is allowed into the first fluid delivery line. Similarly, dry or externally lubricated vacuum massage of tissue may be accomplished by tip 234 having a smooth surface.

A feature of the system is that it delivers fluids directly to the patient's skin while simultaneously exfoliating the skin. In an embodiment, the system uses a variety of specially formulated solutions to provide, for example, treatment for hyperpigmentation, dehydration, acne, and photodamage. Patients receive the most benefit when fluids are used to treat their skin-specific conditions that have specifically been tested and approved for use with the system. These fluids also provide a consistent level of quality. Furthermore, these fluids are tested in the system to ensure that they do not clog the system.

Unapproved fluids may not have been tested and have an uncertain quality. They may fail certain quality standards. Unapproved fluids, for example, may not contain active ingredients, may contain an insufficient quantity of active ingredients, may contain entirely incorrect ingredients, may contain improper proportions of ingredients, or may even contain hazardous ingredients. A patient who receives unapproved fluids as part of their microdermabrasion treatment may suffer dangerous consequences to their health, such as unexpected side effects, rashes, allergic reactions, a worsening of their skin condition, or other problem. Unapproved fluids, because they have not been tested in the system, may also clog the system.

In a specific implementation, the system includes a mechanism for extracting matter from formations on the skin, including comedones (e.g., blackheads or whiteheads), papules (e.g., pinheads), pustules (e.g., pimples), and cysts. In a specific implementation, the system includes a skin incision mechanism to cut the top of the formation (e.g., top of comedone) using the hand piece. Specifically, a user can press a button or engage a mechanism that allows for a shallow thin cut in the top of the area of skin that allows the hand piece to remove the comedone. This feature allows for improved extraction during a microdermabrasion procedure.

In a specific implementation, the system includes a release mechanism for a treatment tip of the handpiece. In specific implementations, a post that the treatment tip (e.g., bristled brush, abrasive pad coated with diamond particulates or dust, or others) inserts upon is mounted on a spring which would lock in place once depressed by a user. A tip holder is inserted over the tip for using during a microdermabrasion procedure. Once the procedure is done, a button located on the handpiece can be depressed, which releases the spring and causes the treatment tip to eject. The tip holder can also eject along with the treatment tip.

Figure 3:
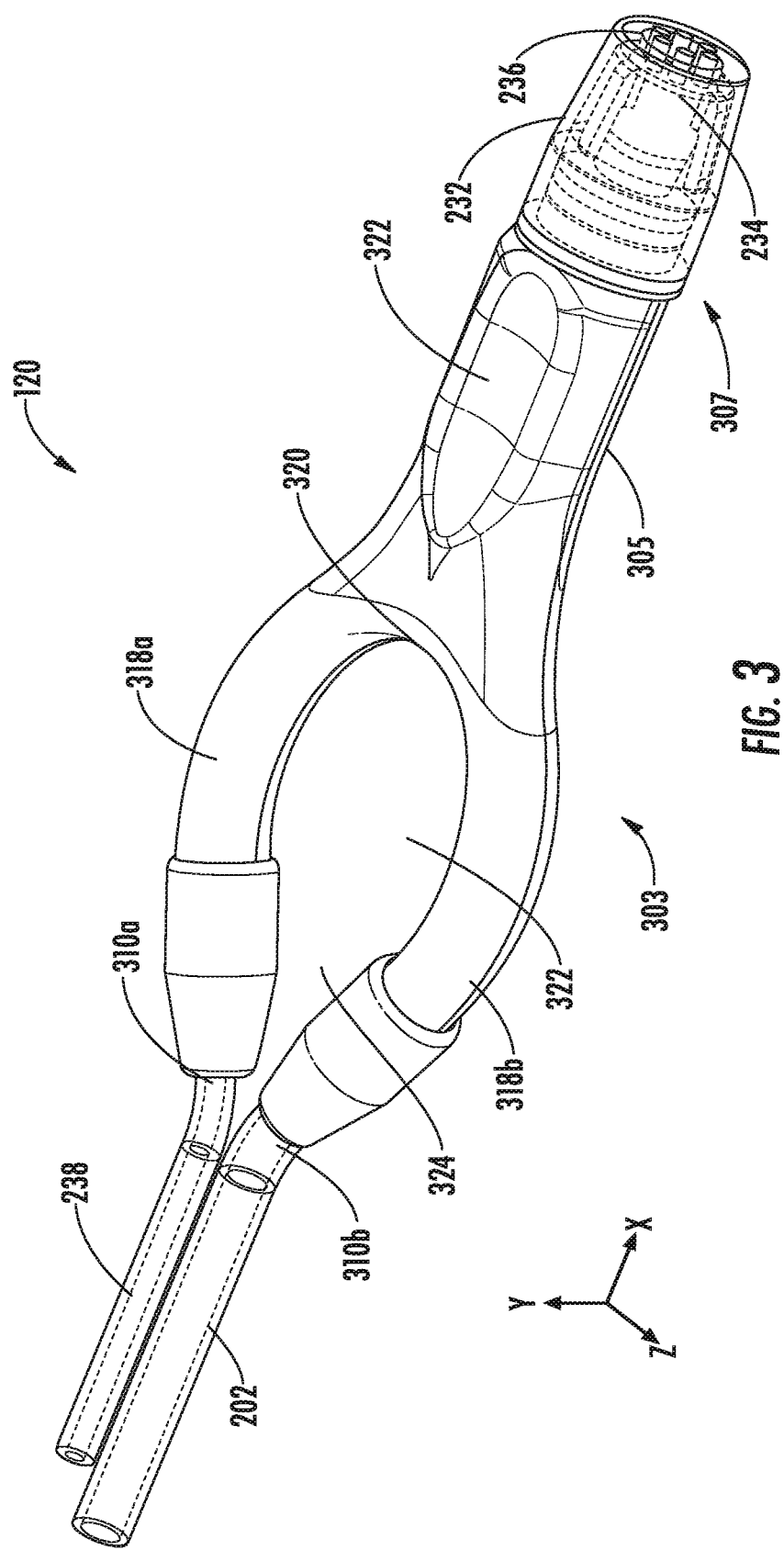
FIG. 3 shows a specific implementation of a hand piece.

FIG. 3 shows a specific implementation of a hand piece 120. The hand piece has a handle portion 303 and a tip portion 307. The handle portion is connected to the tip portion, which is at a distal end of the hand piece. At an opposite end to where the handle is connected to the tip, the handle has two ends, each connected to tubing. In a specific implementation, a first tubing 238 connects to a first end of the handle and conducts fluid to and through an internal channel (not shown) in a first arm 318b of the handle. A second tubing 202 connects to a second end of the handle and conducts fluid to and through an internal channel (not shown) of a second arm 318b of the handle. Arms 318a and 318b connect and join (e.g., merge) into a central handle section 305 of the handle.

The tip portion includes a treatment tip 234 and a tip holder 232. In a specific implementation the tip holder holds the treatment tip. At a tissue-facing end of the tip holder, the tip holder includes an opening 236, through which a portion of the treatment tip is exposed. The opening can contact a targeted area of skin and draw up a central portion of the targeted area of skin to come into contact with the treatment tip.

Fluid from tubing 202 and 238 pass through internal passage ways connected at the ends of the handle, pass through arms 318a and 318b and central handle section to the tip. The fluids can include liquids or gases, or both. For example, tubing 238 may be used to deliver liquid to the tip, while tubing 202 may be used for suction (e.g., vacuum tube) to draw waste materials (e.g., abraded skin particles and fluids) away from the tip.

In a specific implementation, a length of the central handle section and the arms is longer than the tip portion. Between arms 318a and 318b is a gap 322. In FIG. 3, this gap has generally an oval shape and is open at a point 324 between the two arms. In other implementations, the shape of the gap can vary such as a circle or an ellipse. A width from arm to arm (along the z-axis, and parallel to a front surface of the tip) can vary at various points within the gap. A maximum or greatest width from arm to arm is wider than a width of the central handle section. For example, a maximum width can allow a user to insert easily at least one finger or maybe two or more (e.g., index or middle finger, or both) through the gap.

A length of the gap (parallel to a longitudinal axis of the central handle section) extends from a first gap end 320 to a second gap end 324. Typically, the first gap end is closed while the second gap end is open. The width from arm to arm increases in a first direction from the first gap end to a point between the first gap end and the second gap end. At this point, the width of the gap is maximum width from arm to arm. The width decreases in the first direction from the point of maximum width to the second gap end. The shape of the gap can allow a user to easily keep at least one finger through the gap, and to control the hand piece (e.g., pulling away from the skin, and gliding the hand piece across the skin) without the fingers slipping out of the gap at the open end of the second gap end.

The arms are joined together at the central handle section. Typically the central handle section has a greater cross sectional area than each of the arms individually. An exterior surface of the central handle section is generally rounded, but can include a flattened finger region 322. This flattened finger region 322 can include a concave section than can conform to for example, a pad of a finger.

In a specific implementation, the finger region is positioned on a surface of the central handle section that is coplanar with an area defined by the gap between the two arms. For example, the finger region is symmetrical with respect to a longitudinal plane of symmetry of the central handle section. In other implementations, the finger region may be offset (e.g., shifted to the left or to the right of the plane of symmetry).

The finger region can be nearer to the tip of the hand piece to allow for control. For example, a user grips close to the tip of the hand piece while gliding the hand piece across a patient's skin. The proximity to the area to be treated can allow the user to make fine and controlled movements with the hand piece.

In a specific implementation, the hand piece has a central handle section which facilitates grasping by a user. The hand piece includes a tip portion at a distal end of the central handle section. A tip holder 232, in a specific implementation, holds a bristled tip 234. In other implementations, the tip may not be a bristled tip. Instead, other types of tips may be used including, for example, tips with abrasive particles, abrasive disks, tips without bristles, and tips with smooth surfaces.

The dimensions of the central handle section can vary depending on the size of the user's hand, the handedness of the user, the circumstances of use, personal preference, comfort, and other factors. For example, users with small hands require a handle that has an appropriately small girth or circumference (i.e., slimmer) to allow for a comfortable grip. Similarly, a length of the handle can be shortened, to allow the user's finger or fingers to rest comfortably near the tip of the hand piece. In other cases, the handle can be longer and have a larger girth or circumference.

In implementations, as shown in FIG. 3, the central handle section is cylindrical. A cross section of this handle will have a circular shape. In other implementations, the handle is not a cylinder. A cross section will have another shape (e.g., triangle, square, rectangle, pentagon, hexagon, octagon, oval, or ellipse).

In a specific implementation, the central handle section has a length from about 1.5 inches to about 3 inches. In another implementation, the central handle section has a shorter length from about 0.5 inch to about 1 inch. A shorter handle can provide more control that a hand piece with a longer handle. For example, the user's fingers can grip the hand piece closer to the tip with the short handle. Furthermore, a hand piece with a longer handle can be heavier and more cumbersome to use. However, a user with large hands may prefer such a hand piece because it will be more comfortable to use than a hand piece with a short handle.

In a specific implementation, the first and second arms form a concave gap, with an open end having an opening that faces away from the tip of the hand piece. A user can insert one or more fingers (e.g., only the index finger, the index finger with the middle finger, only the middle finger, the index finger with the middle finger and ring fingers, or all these fingers with the pinky finger) through the opening to rest one or more fingers on a closed end of the concave gap, opposite the open end. The point at which the arms are joined together at the central handle section can be referred to as a fork, branching point, groove, recess, cradle, base, or intersection.

In a specific implementation, as shown in FIG. 3, the first and second arms are curved about an axis perpendicular to a longitudinal axis of the central handle section. The first and second arms each terminate at first and second ends, to form a concave gap with an opening. The concave gap can have a length that extends from the closed end to the open end of the gap. For example, if the gap has a short length, the gap will be more shallow than if the gap has a longer length. The first and second legs can have the same length, or different lengths from each other. For example, the first leg can be longer than the second leg so that the first leg can provide more support for a user's hand.

As discussed above for FIG. 2, a first fluid delivery line 238 connects the hand piece 120 to a fluid reservoir 228. The fluid delivery line connects to the hand piece at one of the first or second arms via a first opening 310a. A vacuum line 202 connects to the hand piece at the other arm via a second opening 310b. The fluid delivery line and vacuum line include tubing that delivers treatment fluids to the hand piece, and draws waste materials (e.g., abraded skin particles and optionally, fluids) away from the hand piece, respectively.

This positioning of the tubing, at the end of the hand piece away from the tip, keeps the tubing from interfering with the user's operation of the hand piece at the tip. This allows the user's fingers the freedom to grasp the handle portion without being crowded by openings, ports, or tubing. Furthermore, the tubing will not interfere with the patient or the patient's skin, by dragging along or brushing against the skin.

In a specific implementation, ends of the first and second arms are connected to form a closed polygon shape. For example the polygon can be in the shape of a circle, an oval, or any other closed shape (e.g., ellipse, square, rectangle, triangle, or trapezoid). The user can insert one or more fingers (e.g., the index finger, middle finger, ring finger, pinky finger, or any combination of these) through the polygon to use the hand piece. This configuration can provide additional support for the top side of the user's hand (e.g., the area around the knuckle of the fingers). In this closed configuration, the vacuum line and fluid delivery line can connect to the hand piece at any point on the polygon or along the central handle section. For example, one or more openings or ports are positioned on the polygon to connect the fluid delivery line and vacuum line to the hand piece.

In a specific implementation, the gap between the arms can be a curved shape. In implementations, the closed end of the gap is narrow, so that only a single finger fits comfortably therein (e.g., the index finger or the middle finger). For example, a base of the index finger can rest at the closed end, a bottom of the index finger rests on the central handle, and the thumb and middle finger can also rest on the central handle to grip the hand piece. In another implementation, a user can insert the middle finger into the opening, rest the base of the middle finger at the closed end of the gap, and rest the bottom of the middle finger on the central handle. In other implementations, the closed end can be more wide, to accommodate more than one finger (e.g., one, two, three, or four fingers).

In a specific implementation, the gap is formed in a proximal end, opposite the tip, of the central handle section. For example, the proximal end of the handle includes an indentation (or groove, recess, or cutout), which provides a base for the user's finger or fingers to rest in.

In other implementations, the first and second arms are not curved. Rather, the first and second arms extend horizontally away from each other, forming a bar that is transverse to the central handle section. In this configuration, the user rests one or more fingers on the bar, which supports the bottom of the one or more fingers.

In a specific implementation, the first and second arms are coplanar with the central handle. In other implementations, the arms are not coplanar and can be angled with respect to the central handle. For example, an angle between a plane of the arms and that of the elongated handle can range from about 130 degrees to about 179 degrees. Such an angle in the hand piece can allow the user to hold and use the hand piece in different positions, and at different angles.

In implementations, the first and second arms are symmetrical about a longitudinal axis of the central handle. Further, the girth or circumference of each of the arms can be the same or similar. A symmetrical configuration can provide a balanced feel for the user.

In other implementations, the arms are asymmetrical and can each have a different shape, dimension, girth, or circumference from the other arm. For example, the first arm can have a wide curvature near the closed end of the gap while the second arm has a narrower curvature. One arm can be longer than the other, so that the longer arm can extend around more of a user's hand to support it. One arm can have a greater girth or circumference (i.e., thicker) than the other arm in order to fit in a naturally larger gap between fingers.

For example, the gap between the thumb and index finger is naturally a larger gap than the gap between the index finger and middle finger, or the gap between the middle finger and the ring finger. Therefore, an implementation of the hand piece can include a first arm that is thicker than a second arm. This configuration can be more comfortable to use.

In specific implementation, the second arm of the hand piece, having a vacuum tubing extending therethrough, has a maximum diameter that is greater than a maximum diameter of the first arm having a fluid delivery tubing.

Many other implementations are possible. The dimensions may vary considerably depending on the size of the user's hand, the handedness of the user, how the hand piece is to be used, comfort of the user, other factors, or a combination of these. For example, users with small hands would require a small hand piece with a shorter elongated handle portion, and slim arm portions. In yet another example, the dimensions of the hand piece are tailored for users who are either right-handed or left-handed.

In a specific implementation, the central handle section includes an indentation 322 (or a depression, notch, or groove) positioned on the handle to allow the bottom side of the index finger to rest in. The indentation can be a circular, oval-shaped, oblong-shaped, or another shape to conform to the contours of the index finger. In other implementations, the indentation can include a textured pad to provide additional grip for the index finger. For example, the pad can include a rubber material with raised rails or other projections that provide a padded and slip-resistant surface for the user to grip. In other implementations, the projections are formed in a raised pattern on the pad. In yet another implementation, the pad includes depressions or grooves in the pad.

In a specific implementation, a rubber sleeve is placed over the central handle. The rubber sleeve provides a secure surface for the user to grasp. The surface of the sleeve can also be textured, knurled, or both, in order to provide a slip-resistant surface.

The central handle can include one or more additional indentations for other fingers (e.g., the thumb, and middle finger) to rest in. These can be positioned on side surfaces of the central handle. These indentations can also have textured grip pads for additional support. In other implementations, the indentation is omitted from the central handle, which provides a smooth surface for the user's hand.

In a specific implementation, to perform microdermabrasion, a user holds the hand piece and applies the treatment tip to a patient. In a specific implementation, the user rests the base of the index finger at the closed end of the gap, where the first and second arms join with the central handle. The closed end supports the base of the index finger, while other fingers can rest on the central handle. The handle can have a length that is about as long as, or longer than, the length of the index finger so that the index finger can rest and extend along the handle. The user can grip the handle with the tips of the index finger, thumb, and middle finger.

In a specific implementation, the first and second arms are positioned to curve around either side of the index finger. This curvature creates supports for the base of the index finger, and prevents the finger from slipping while the user uses the hand piece. The opening of the gap allows the user to easily insert and remove the index finger (or other fingers, or a combination) through and from the hand piece.

Microdermabrasion treatment sessions can last for long durations of time. Throughout the day, the user's hand can tire easily from gripping the handle for several hours at a time. With the system, the base of the finger or fingers is supported by the gap formed by the first and second arms. This configuration provides the user with control over the hand piece. The fingers are positioned close to the tip of the hand piece, which can allow the user to make small, fine movements. The configuration also allows the user to focus less on tightly gripping the handle with the tips of the fingers. Thus, the user will be comfortable using the hand piece, even after several hours of use.

There are numerous techniques on how a user can apply the hand piece and treatment tip to perform microdermabrasion. For example, one approach is draw the tip across the skin of the patient in a single direction, generally away from the center or nose of the patient's face (when working on the patient's face). Another approach is to use a scrubbing motion, moving the tip back and forth on the face.

One of ordinary skill in the art will appreciate that many different shapes and materials may be employed for the hand piece and the system is not to be limited to an elongated, substantially cylindrical handle as shown. In the example of FIG. 3, the central handle section and first and second arms are made of plastic, such as nylon or other plastic having sufficient toughness and mechanical strength, but may also be made of metal, such as stainless steel or aluminum, for example, or ceramics or composites such as carbon fiber. The handle may include a combination of materials. For example, a rubber sleeve may be placed over the central handle which may be made of plastic. The rubber sleeve provides a secure surface for a user to grasp. The surface of the handle may also be textured, knurled, or both in order to provide a slip-resistant surface.

Fluid delivery line 238 may be flexible and may be made of polyvinyl chloride (PVC) or other compatible plastic or polymer, for example. Similarly, all other vacuum lines (e.g., vacuum line 202) described herein are flexible to afford maneuverability to hand piece 120 and may be made of PVC or other compatible plastic.

These and other components of a microdermabrasion hand piece are discussed in U.S. Pat. No. 6,695,853, filed Nov. 21, 2001, and issued Feb. 24, 2004 which is incorporated by reference. This patent application incorporates by reference U.S. Pat. No. 6,695,853, filed Nov. 21, 2001, and issued Feb. 24, 2004; U.S. Pat. No. 7,658,742, filed Mar. 19, 2003, and issued Feb. 9, 2010; U.S. Pat. No. 7,951,156, filed Nov. 22, 2006, and issued May 31, 2011; U.S. Pat. No. 8,236,008, filed Feb. 29, 2008, and issued Aug. 7, 2012; U.S. Pat. D648,025, filed Feb. 29, 2008, and issued Nov. 1, 2011; U.S. Pat. D616,094, filed Jul. 29, 2008, and issued May 18, 2010; U.S. Pat. D612,939, filed Jul. 29, 2008, and issued Mar. 30, 2010; and U.S. patent application Ser. Nos. 12/197,047, 12/197,065, and 12/197,075, filed Aug. 22, 2008; Ser. No. 13/569,022, filed Aug. 7, 2012; and Ser. No. 12/645,210, filed Dec. 22, 2009. Any feature or combination of features described in the above applications can be used in combination with (or in substitution or replacement of) features described in this application.

Figure 4:
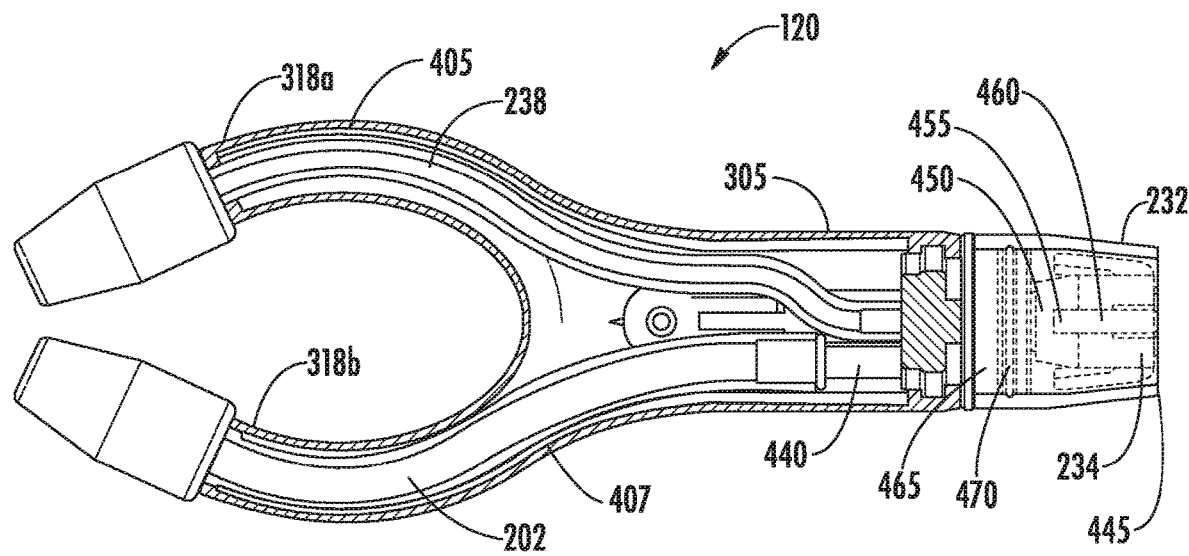
FIG. 4 shows a cross-section of a specific implementation of a hand piece.

FIG. 4 shows a cross-sectional view of hand piece 120. For use in microdermabrasion, the hand piece is positioned such that tip holder 232 contacts the skin surface to be microabraded. Vacuum source 226 (see FIG. 2) is turned on to establish a vacuum within the system. The order of positioning and turning on the vacuum source 226 is not critical as it can be turned on prior to contacting the tip holder 232 to the skin.

With reference to FIG. 2 and FIG. 4, when the vacuum source is turned on, a targeted area of the skin is drawn up into opening 445 and a central portion of the targeted area of skin is drawn into contact with bristled tip 234. At the same time, fluids in fluid reservoir 228 are drawn through fluid delivery line 238 and into the hand piece through the first arm 318*a*. The fluids flow through the fluid delivery line, positioned in a passageway 405, through the bristled tip, through an opening on the bristled tip and finally out opening 445 where the fluids treat the skin.

The fluids then reenter opening 445 and pass through a vacuum created in a space 440. The fluids now carry with it the exfoliated skin particles and any other waste that was removed through the microdermabrasion process. The fluids travel within vacuum line 202, positioned in a passageway 407, and are collected in the collection reservoir 208. The vacuum created allows there to be little to no spent fluid or debris that must later be cleaned from the skin.

As the user glides the tip holder over the skin, the bristled tip is scraped over the skin wherein microdermabrasion of that portion of the skin is performed.

In a specific implementation, a male to female connection between the bristled tip and the central handle 305 acts as a helpful guide to properly position the bristled tip to the handle. In a specific implementation, a distal end 450 includes a cavity that forms a female core which fits onto a protrusion 455 of the bristled tip. The bristled tip may then include a male protrusion, opposite the bristles, that forms a male core which fits into the female core of the distal end. The bristled tip fits onto the distal end using, for example, an interference or press fit. However, in other implementations, other attachment mechanisms may be used. For example, the distal end may include a tab to create a snap fit between the distal end and the protrusion of the bristled tip. As another example, the bristled tip may thread onto the distal end.

Figure 5:
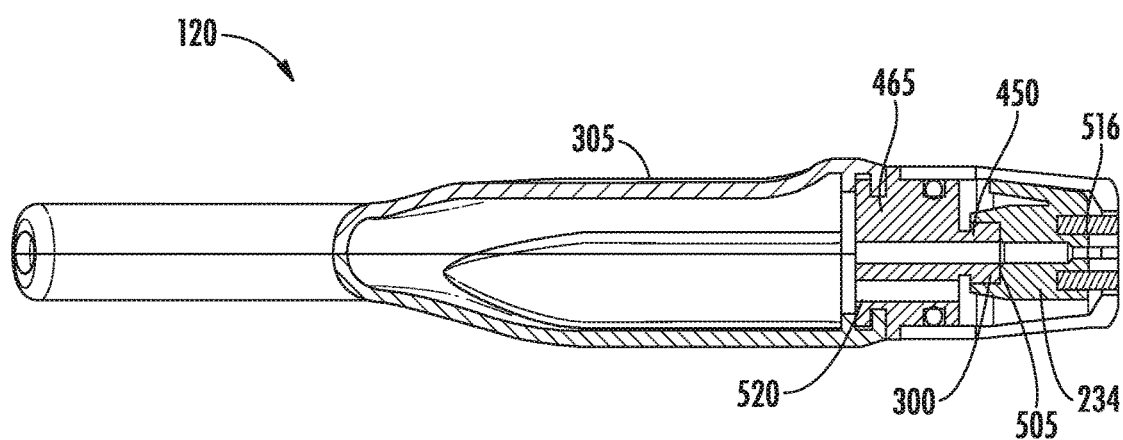
FIG. 5 shows another cross section of a specific implementation of a hand piece.

In other implementations, as shown in FIG. 5, the bristled tip includes a cavity 505 that forms a female core which fits onto a distal end of a cannula 300. That is, the distal end forms a male core which fits into the cavity.

The bristled tip also includes an internal passageway 460, which is coupled to a first opening at one end of the bristled tip and a second opening at the opposite end of the bristled tip. This allows fluids to pass through the bristled tip using the passageway 460, and eventually exiting at the opening.

Tip holder 232 fits over the bristled tip and onto vacuum head base 465. In a specific implementation, one or more O-rings 470 or other sealing members (e.g., gasket) may be provided between the vacuum head base and the tip holder to facilitate the pressure tight seal. The tip holder may be friction fit, provided with threads, or both, or another attachment means may provide a pressure tight fit between the components. For example, a snap fit such as an annular snap fit may be used. Alternatively, the tip holder may be integrally machined or molded with the vacuum head base. In another implementation, the bristled tip may be integrally machined or molded with the tip holder.

FIG. 5 shows another cross-sectional view of a specific embodiment of the hand piece. When a vacuum source (see reference 226 in FIG. 2) is turned on, fluids are pulled through the fluid delivery line of a passageway, positioned in the first arm of handle 305. The fluids flow through the vacuum head base 465, the bristled tip 234, and exit at an opening 516 on the bristled tip. The fluids exit at the opening and treat the skin. A vacuum created pulls the fluids back into the tip where the fluids move past the outside of bristled tip. The fluids are pulled into a vacuum line positioned in a passageway of the second arm and are collected in collection reservoir (see reference 208 in FIG. 2).

Figure 6:
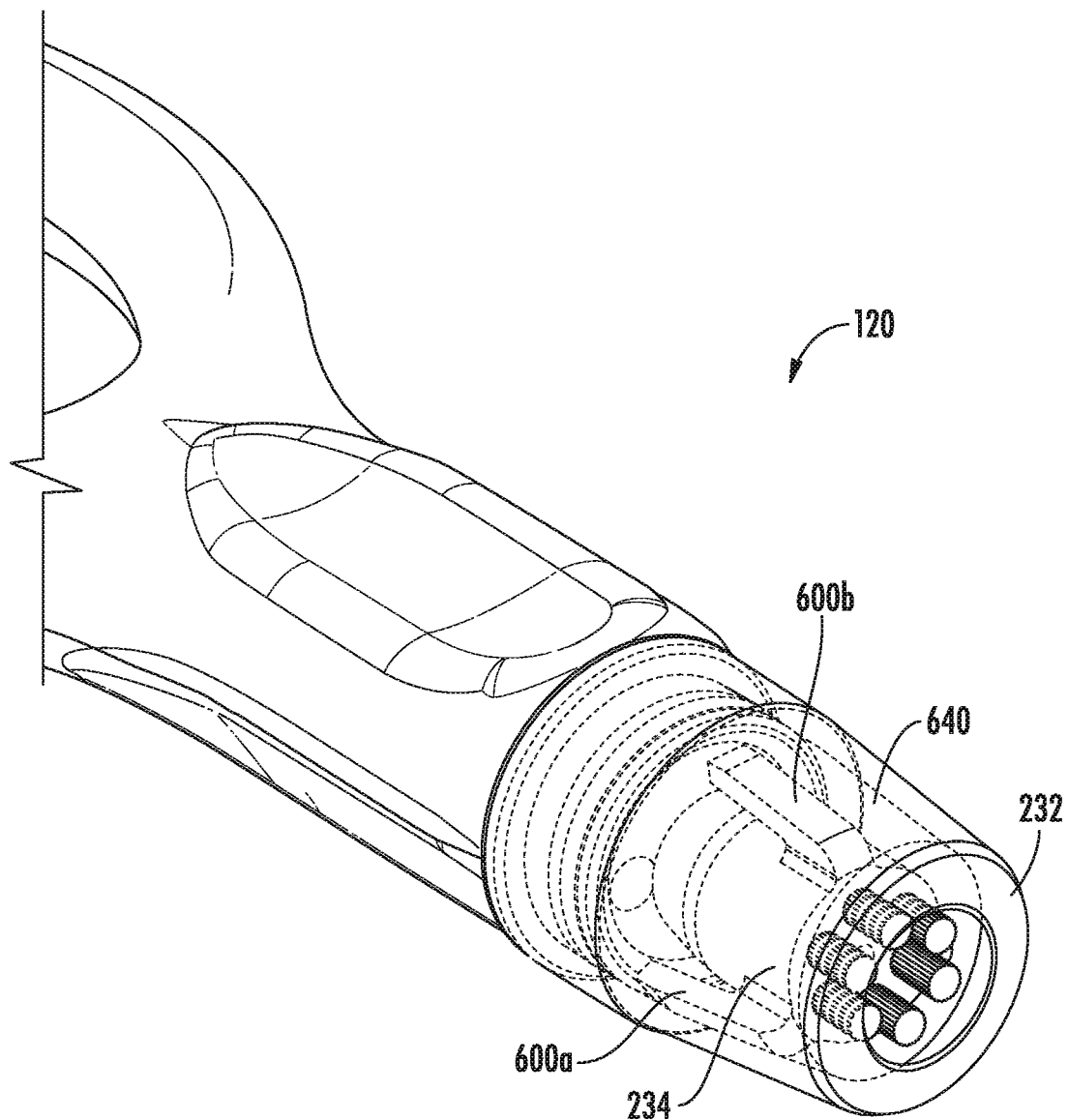
FIG. 6 shows a perspective view of a specific implementation of a hand piece with a bristled tip and an elongated handle.

FIG. 6 shows a perspective of the bristled tip and central handle 305 In a specific implementation, the bristled tip includes support ribs 600*a*, 600*b*, and 600*c* (not visible).

When the tip holder is fitted over the bristled tip, the support ribs connect with the inner surface of the tip holder. The support ribs help to support and stabilize the bristled tip in the tip holder. The support ribs help to ensure that the bristled tip is properly aligned in the holder. Fluid can flow through the tip, treat the skin, and be vacuumed back into the tip holder.

In a specific implementation, the support ribs are attached such that they are initially flush with a front face of the bristled tip. However, in other implementations, the support ribs may be attached such that they are offset from the front face of the bristled tip. Support ribs extend outwardly and then turn to extend longitudinally down the length of the bristled tip and at an angle such that their tips are splayed. The angle may match the interior surface angle of the tip holder. This allows support ribs to contact the inner surface of the tip holder for support and stabilization.

When the tip and tip holder are assembled together, the support ribs touch an inside surface of the tip holder and help form annular space 640. Specifically, the annular space is formed between the inner surface of the tip holder and exterior surface of bristled tip. Generally, the less volume or space taken up by the ribs enlarges the volume of the annular space.

In a specific implementation, fluids and abraded tissues are vacuumed back into the hand piece through the annular space. This annular space creates an annular vacuum region that surrounds the passageway of the hand piece where fluids flow to the tip. The volume of the annular space may vary depending on the specific design, but generally, larger volume annular spaces will help prevent potential blockage or other similar problems, especially when compared to pores or other structures that will restrict flow more.

The support ribs also help to ensure that the bristled tip is properly aligned so that fluid can flow through, treat the skin, and be pulled back into the tip holder.

In a specific implementation, the support ribs are positioned at equal distances from each other around the bristled tip. For example, the support ribs may be placed at 60 degree angles from each other as shown. However, in other cases, the support ribs may not be equally positioned in relation to each other. It should be appreciated that any arrangement or number of support ribs (including no support ribs) is possible so long as the fluids are able to pass from the front of the tip holder to the back of the tip holder.

Consequently, a flange, or a portion of a flange may be used between the bristled tip and the tip holder either with or without one or more support ribs. For example, where a flange completely encircles the bristled tip, the flange may contain one or more openings which allow fluids to pass from the front of the tip holder to the back of the tip holder.

In a specific implementation, there may be a total of three support ribs as shown in FIG. 6. However, in other implementations there may, for example, be four support ribs. In yet another implementation, there may be no support ribs, one, two, five, or more than five support ribs.

In a specific implementation, the tips of the support ribs may have beveled edges. These beveled edges allow the tip holder to easily slide on and off over the bristled tip.

In a specific implementation, the support ribs are molded or machined as an integral part of the bristled tip as shown. In other implementations, the support ribs are molded or machined as an integral part of the tip holder. For example, the interior surface of tip holder may contain one or more protruding support ribs that contact bristled tip when the tip holder is placed over the bristled tip. In yet another implementation, there may be a combination of support ribs which may be molded or machined as an integral part of the tip holder and bristled tip.

The tip holder is smooth surfaced and adapted to glide over the skin as fluids (e.g., lotions, conditioners, vitamins, oils) exit the hand piece to treat the skin. The tip holder and treatment tip (e.g., bristled tip) may, for example, be impregnated with polytetrafluoroethylene (PTFE), treated with wax, or include other hydrophobic ingredients to ensure that fluids do not adhere to the tip holder and treatment tip.

The tip holder and treatment tip of the hand piece may be made of metal (e.g., stainless steel, aluminum, titanium, brass) or plastic such as nylon, thermoplastics, polyethylene, polycarbonate, acrylonitrile butadiene styrene (ABS), or Delrin. Glass, such as Pyrex, for example, may also be used. The tip holder may be, although not necessarily, transparent or translucent. A transparent tip holder may allow better visualization by the operator during use.

The treatment tip and tip holder of the system (in the various embodiments described and shown in this application) are designed to be removable and installable by the user. Further, the user can dispose of used or old tips or holders, or both, and easily replace them with new (or clean) ones. Also, the user can remove the tips to clean them or clean the passages to ensure the flow, vacuum and fluid, are clear, so that the microdermabrasion device will be operating at full efficiency. Also, in an embodiment, the tip and tip holder are designed to be low cost (e.g., made of less expensive materials) and disposable.

The design may be such that the tip wears faster than the tip holder. So users may stock up with greater numbers of replacement tips than holders. When a tip wears out, the user replaces the tip without needing to replace the holder. This is analogous to the situation of replacing an ink refill insert of a pen. For example, the holder may be replaced once for every seven (or other number) of tips. This lowers the cost of use for users, because the tip, which needs more frequent replacement because it is subject to more wear and tear, is replaceable separately from the tip holder.

Figure 7:
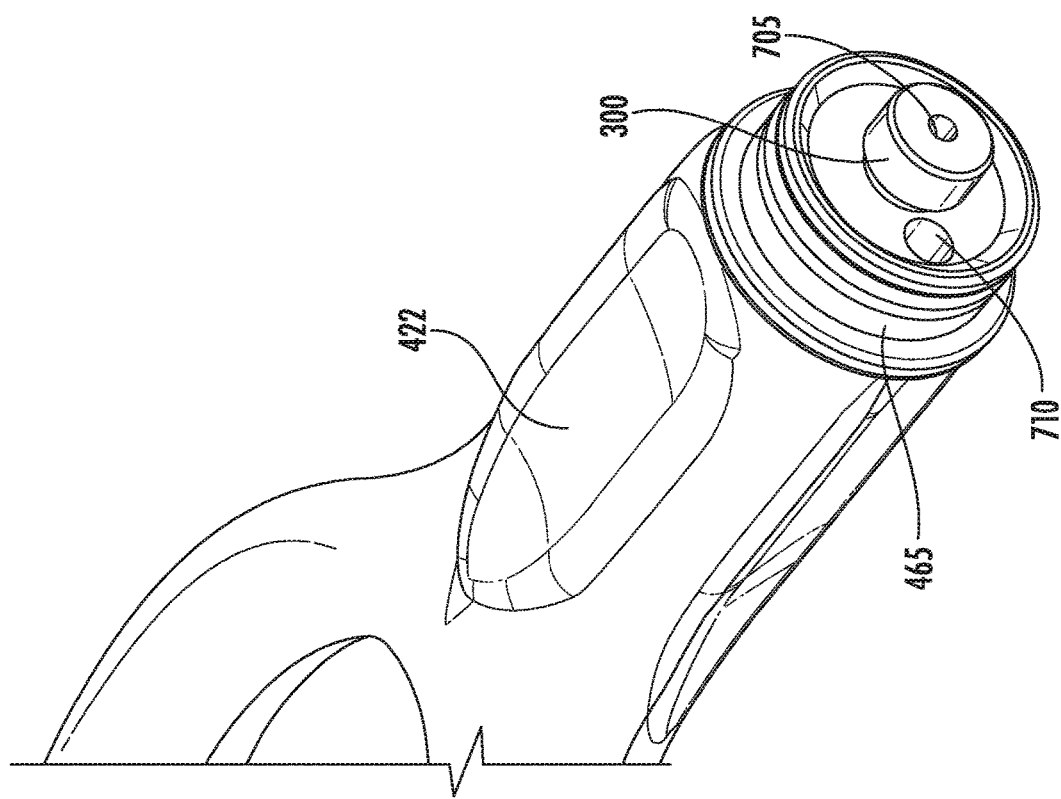
FIG. 7 shows a perspective view of a specific implementation of a hand piece without a bristled tip and a tip holder attached.

FIG. 7 shows a perspective of a hand piece without a bristled tip and a tip holder attached. The distal end of the cannula 300 and the vacuum head base 465 shown in greater detail. In this implementation, as described in the description for FIG. 5 above, to attach the bristled tip to the vacuum head base, the bristled tip (not shown) includes a cavity that forms a female core which fits onto the distal end of the cannula.

When a vacuum source (see reference 226 in FIG. 2) is turned on, fluids are pulled through the fluid delivery line of a passageway, positioned in the first arm of the central handle. The fluids flow through the vacuum head base, through the fluid delivery line positioned in a first passageway of the vacuum head base, and are delivered to the bristled tip via a first opening 705. The fluids exit bristled tip and treat the skin. A vacuum created by a vacuum line pulls the fluids back into the tip where the fluids move past the outside of bristled tip. The fluids are pulled from the bristled tip into a vacuum line, through a second opening 710 of the vacuum head base. The fluids then flow through a vacuum line positioned internally in the vacuum head base, the elongated handle, and the second arm of the hand piece, out of the hand piece to a collection reservoir (see reference 208 in FIG. 2).

In a specific implementation, the central handle includes an indentation 422 (or a depression, notch, recess, or groove) positioned on the elongated handle to allow the bottom side of the index finger to rest in. The indentation can be a circular, oval shaped, oblong shaped, or a combination of these to conform to the contours of the bottom side of the index finger. In the implementation shown here, a first end of the indentation that is closer to the tip of the hand piece is rounded, and a second end, opposite of the first end, is tapered. The indentation includes raised side walls or perimeter surrounding the indentation to keep the index finger from slipping out. In other implementations, the indentation can include a textured pad to provide additional grip for the index finger. The handle can include one or more additional indentations for the thumb and middle finger to rest in. These indentations can have textured grip pads for additional support.

Figure 8:
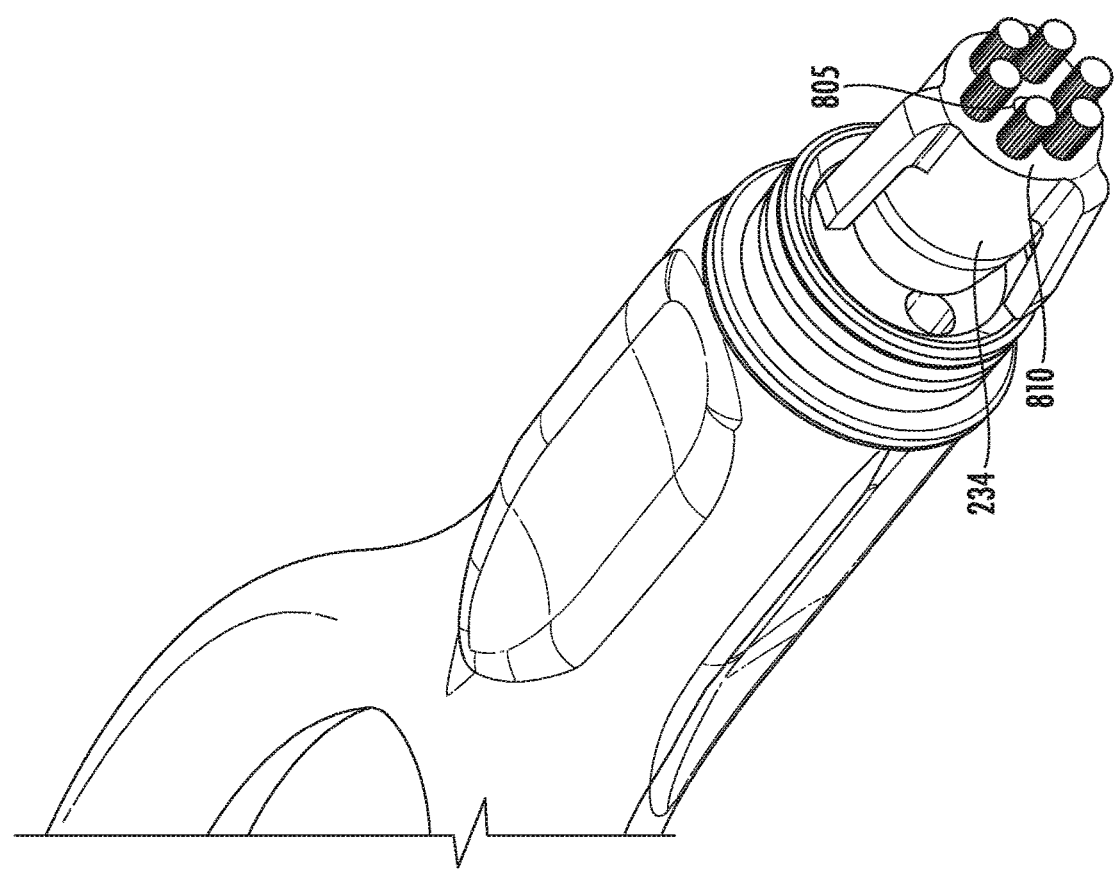
FIG. 8 shows a perspective view of a specific implementation of a hand piece with a bristled tip placed onto a cannula.

FIG. 8 shows a specific implementation of a hand piece with a bristled tip placed onto a cannula. The bristled tip includes six groups of bristles. In another specific implementation there may be four groups of bristles. In other implementations, there may be just one group of bristles, two, three, five, seven, eight, nine, ten, eleven, twelve, or more than twelve groups of bristles.

The groups of bristles form a ring around an opening 805 through which fluid flows out. The bristles separate the opening from the skin so that fluid can flow out of the opening. In a specific implementation, the opening is on the same plane as face 810 of the bristled tip. In other implementations, the opening may be on a different plane. For example, the opening may be recessed into the face or may protrude out from the face. In an implementation where the opening protrudes out, the fluids exit the opening closer to the skin. This helps to ensure that the skin is treated with fluids before the fluids are pulled back (or suctioned) into the tip holder.

In the implementation shown in FIG. 8, the groups of bristles are equally spaced from each other, and surround the opening. However, in other implementations, the groups of bristles may not be equally spaced from each other, may only occupy a certain region of the treatment head, or both. For example, in a specific implementation, bristles may only occupy the top half of the bristled tip. In this specific implementation, the bristled tip may be intended to travel in a specific direction over the skin. For example, if the skin is particularly sensitive then the direction of travel may be such that the leading edge, i.e., the edge that first contacts the skin, is the edge that does not include the bristles. This allows the fluids to contact the skin before the bristles to provide, for example, lubrication or numbing agents. The trailing edge, i.e., that edge that does include the bristles can then contact the patient's skin to provide the microdermabrasion.

In yet another implementation, the opening may be located at a different region of the bristled tip, such as near an edge of the bristled tip. Furthermore, there may be more than one opening through which fluid flows out of. For example, there may be two, three, four, five, six, seven, or more than eight openings for fluid to flow out of. In a specific implementation, these openings may then surround the group or groups of bristles.

In a specific implementation, the bristles are distributed along a planar surface of bristled tip. However, in other implementations, the surface may not be planar. For example, the surface may be convex or concave. The bristles may also be distributed over a helical surface. These nonplanar surfaces may be used, for example, on skin surfaces that are not planar such as the edge of patient's jawline or the curved surface of a patient's forehead. Bristles distributed on a nonplanar surface may be better able to fully contact the patient's skin while maintaining the same level of pressure across all the bristles.

Other characteristics of the bristled tip are discussed in U.S. Pat. No. 8,236,008, which incorporated by reference in its entirety.

Figure 16A:
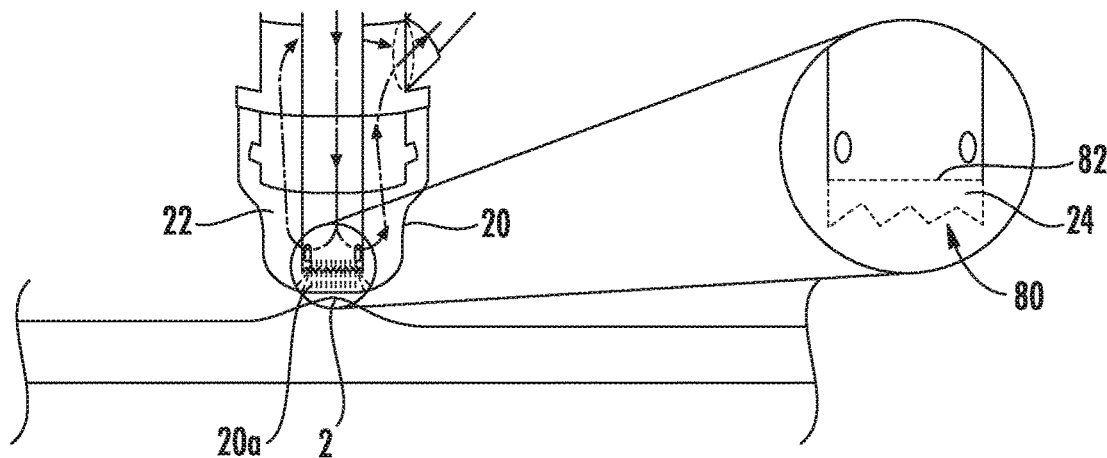
FIG. 16A shows an illustration of a specific embodiment of a treatment tip.
Figure 16B:
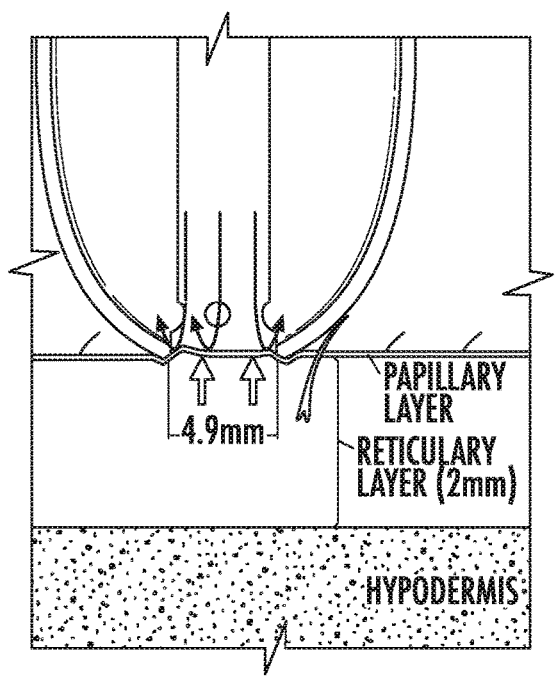
FIG. 16B shows an example of a specific embodiment of a treatment tip in use.
Figure 16C:
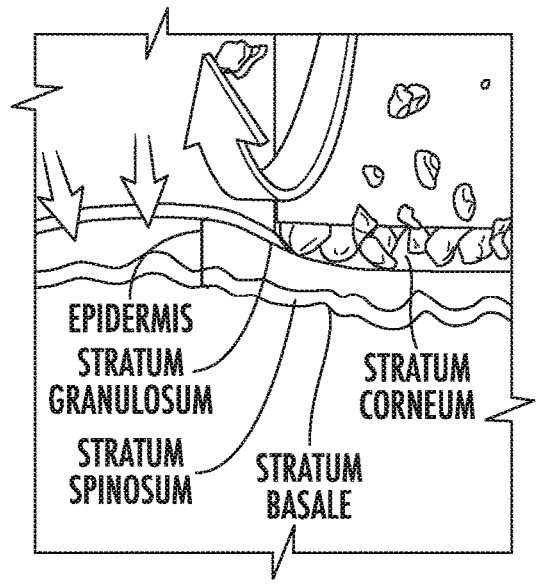
FIG. 16C shows another example of a specific embodiment of a treatment tip in use.

Although a bristled treatment tip is discussed, a wide variety of abrasive tips may be used. This may include, for example, different types of abrasive elements such as bristles, meshes, abrasive particles, or combinations of these. Abrasive tipped devices or rotating brushes and cylinders coated with abrasive particles, can be used to remove skin layers. In a specific implementation, as shown in FIGS. 16A-16C, an abrasive treatment tip is coated with diamond dust on a front surface that faces the skin. The tip can rotate. Many different sizes of tips are available. Thus, small skin surfaces such as the cheek, forehead, chin, and nose may be treated. Large surfaces such as the back, arms, or torso may also be treated.

FIGS. 9A and 9B show a comparison of specific implementations of the hand piece. FIG. 9A shows a hand piece that includes a shorter elongated handle portion than that shown in FIG. 9B. With a shorter handle, a user can grip the hand piece closer to the tip. Thus, a shorter handle can provide the user with more control over the hand piece. In implementations, a length of the shortened elongated handle can range from about 0.5 inches to about 1 inch. In other implementations, a length of the longer elongated handle can range from about 1.5 inches to about 3 inches.

Figure 10:
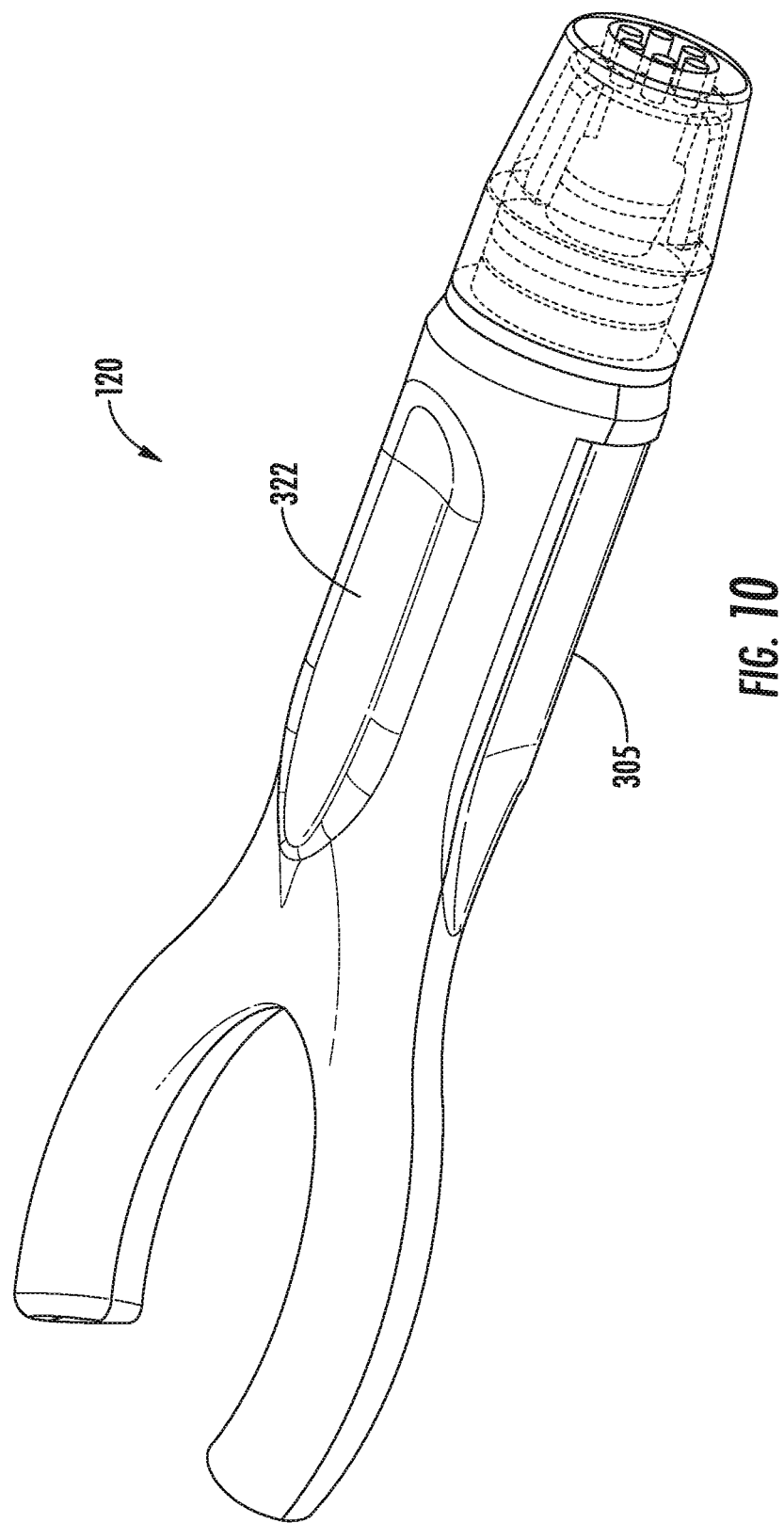
FIG. 10 shows a perspective view of a specific implementation of a hand piece.
Figure 17:
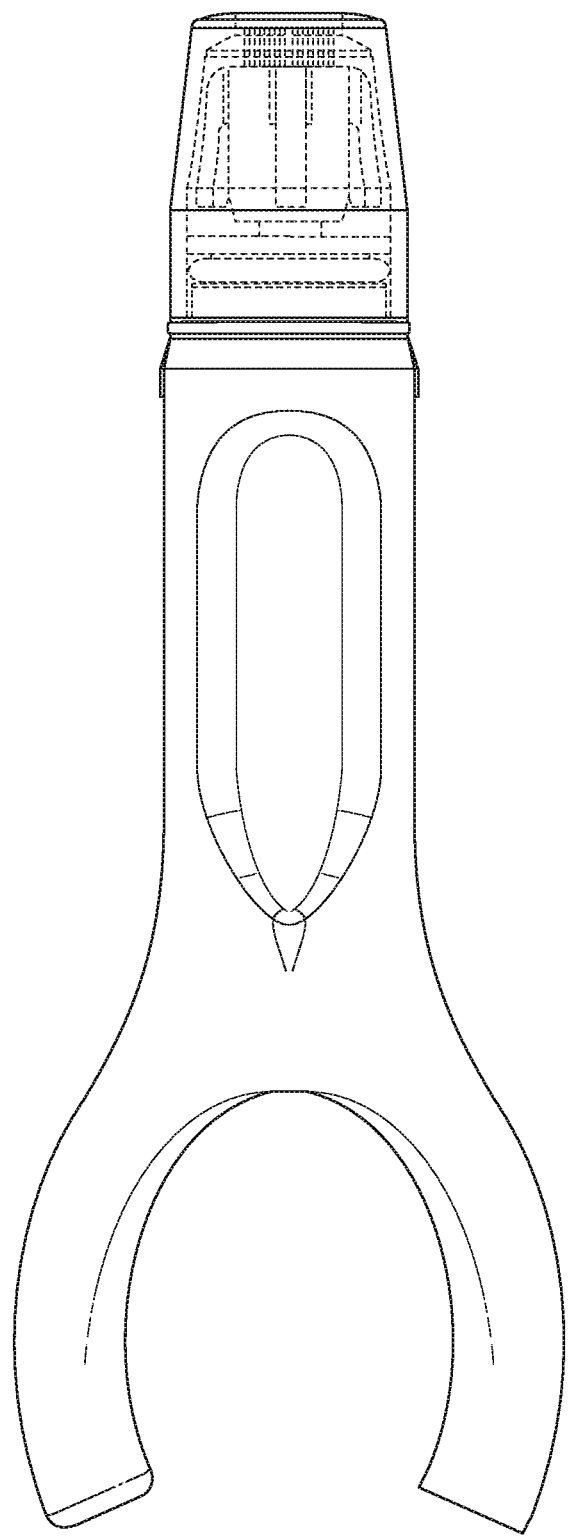

FIG. 10 shows a perspective view of an implementation of the hand piece that includes a long central handle section as described above for FIG. 9B. The structure of the hand piece is the same as the implementation shown in and described above for FIG. 3. In this implementation with a long handle, indentation 322 can be longer than the indentation in a hand piece with a short central handle. Users with larger hands may prefer to use this implementation where the handle can support more of the index. The indentation can be a circular, oval-shaped, or oblong-shaped to conform to the contours of the index finger. In other implementations, the indentation can include a textured pad to provide additional grip for the index finger. The handle can include one or more additional indentations for the thumb and middle finger to rest in, on positioned on side surfaces of the central handle. These indentations can have textured grip pads for additional support.

FIG. 11 shows a top view of a specific implementation of a hand piece. The indentation has an oblong shape to cradle a length of the bottom side of the user's index finger. The indentation can be of any shape and size. For example, the indentation can be a circular indentation to support the bottom of a tip of the index finger only.

Figure 12:
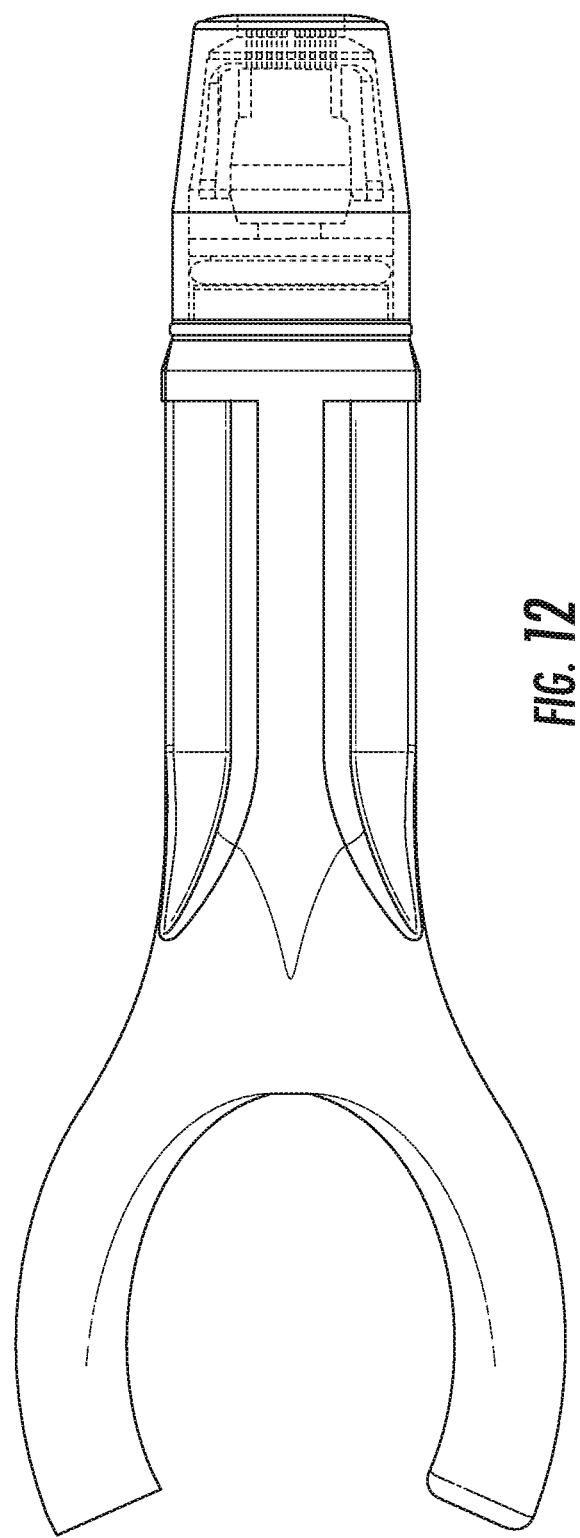
FIG. 12 shows a bottom view of a specific implementation of a hand piece.

FIG. 12 shows a bottom view of a specific implementation of a hand piece. The bottom side can be smooth, without any indentations or grooves.

Figure 13:
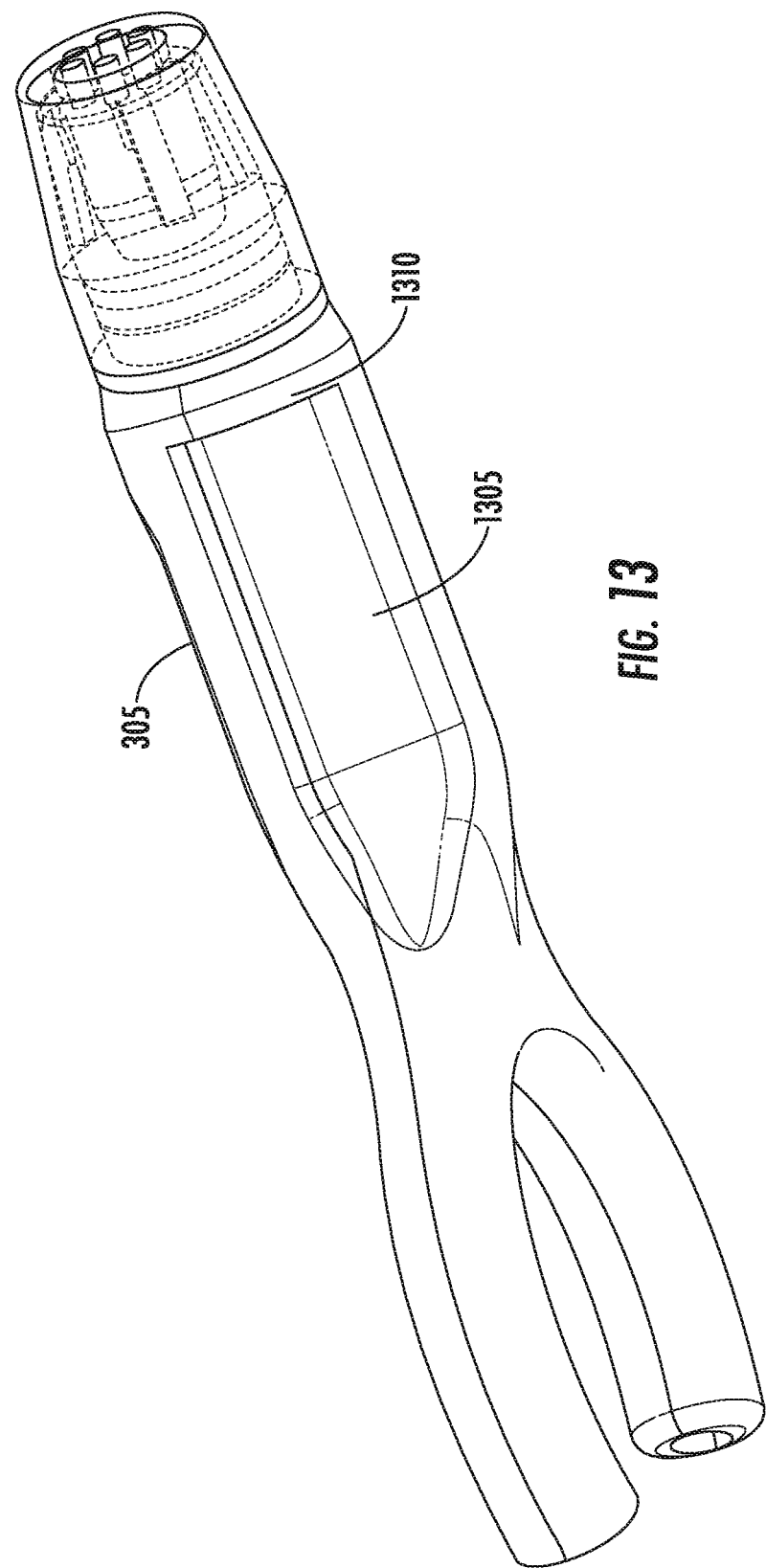
FIG. 13 shows a bottom perspective view of a specific implementation of a hand piece.

FIG. 13 shows a bottom perspective view of a specific implementation of a hand piece. The central handle includes side surfaces 1305 that are substantially flat, where the tips of the middle finger and thumb can rest. The tips of these fingers can rest comfortably on these sides while the user is using the hand piece. A side can support the bottom of the user's middle finger or thumb. The handle can include projections 1310 (e.g., guards, or stops) to prevent the thumb and middle finger from slipping downward while the user is pressing down on the hand piece.

Figure 14:
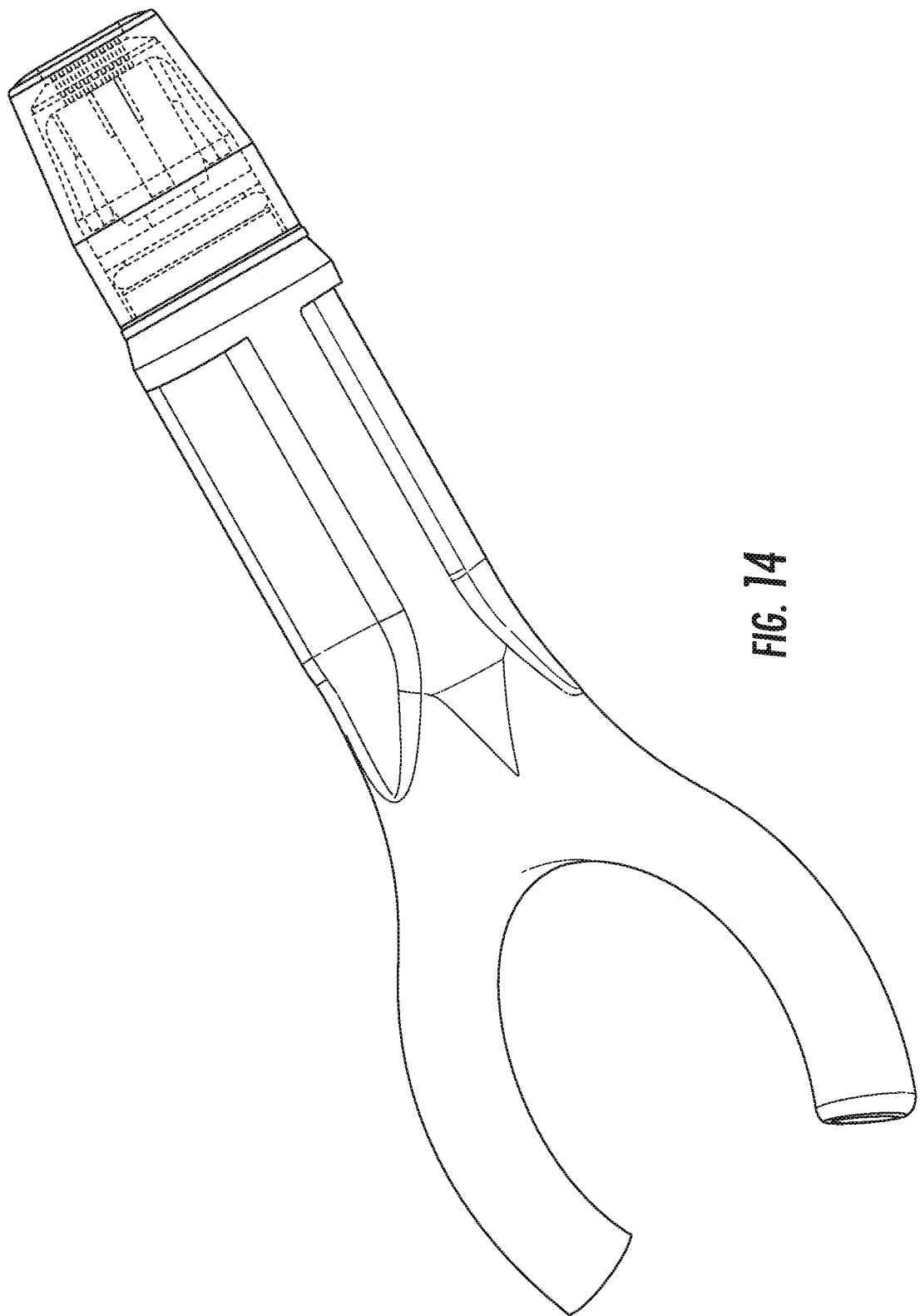
FIG. 14 shows another bottom view of a specific implementation of a hand piece.

FIG. 14 shows another bottom view of a specific implementation of a hand piece.

Figure 15:
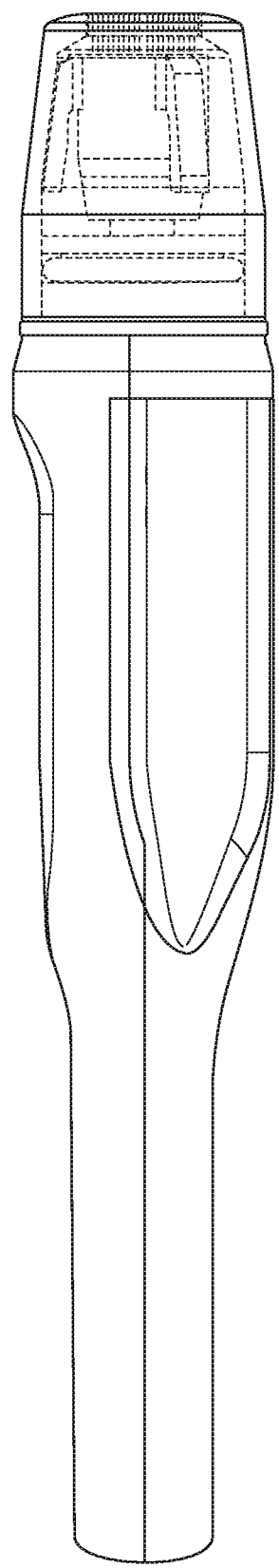
FIG. 15 shows a side view of a specific implementation of a hand piece.

FIG. 15 shows a side view of a specific implementation of a hand piece.

FIG. 16A shows an illustration of a specific embodiment of a treatment tip. The treatment tip can be an abrasive tip 24 coated with particles such as a layer of diamond dust 80. In a specific implementation, the abrasive coated tip (e.g., a diamond head) can be removed from the remainder of the tip. This feature is show by dashed line 82. In other implementations, the abrasive head is not removable and remains integrated with the treatment tip of the handpiece.

In use, a treatment head 20 is placed over the treatment tip. When a vacuum source is turned on, a targeted area of the skin is drawn up into opening 20a and a central portion 2 of the targeted area of skin is drawn into contact with the surface with diamond-coated abrasive or other abrasive particles of the treatment tip. Fluids that carry with it the exfoliated skin particles and any other waste that is removed as they pass through a vacuum 22 created in the tip of the handpiece.

FIG. 16B shows an example of a specific embodiment of a treatment tip (e.g., diamond-coated tip) in use.

FIG. 16C shows another example of a specific embodiment of a treatment tip in use.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A handpiece for a microdermabrasion system comprising:
   a tip, at a distal end of the handpiece, wherein the tip comprises an abrasive element comprising
   a first abrasive element channel opening at a proximal end of the abrasive element,
   a second abrasive element channel opening at a distal end of the abrasive element,
   an abrasive member at the distal end of the abrasive element, and
   a first opening, which is removably coupled to the first abrasive element channel opening;
   a second opening, which is not coupled to the first abrasive element channel opening;
   a tip holder coupled to the tip and the abrasive element, wherein the second opening is between the tip holder and the abrasive element;
   a first portion of a handle of the handpiece coupled to the tip;
   a second portion of the handle, coupled to the first portion;
   a third portion of the handle, coupled to the first and second portions, wherein the second and third portions are separated by a first distance between them;
   a first port, coupled to an end of the second portion, wherein the first port couples to a first internal channel passing through the second and first portions of the handle, and the first internal channel is coupled to the second opening at the tip; and
   a second port, coupled to an end of the third portion, wherein the second port couples to a second internal channel passing through the third and first portions of the handle, and the second internal channel is coupled to the first opening at the tip, and the first opening is separate from the second opening at the tip.

2. The handpiece of claim 1 wherein the first distance between the second and third handle portions is greater than a width of the first portion of the handle.

3. The handpiece of claim 1 wherein the handpiece is symmetrical about an axis line running between the first portion of the handle and between the second and third portions of the handle.

4. The handpiece of claim 1 wherein the first port is to be coupled to a vacuum source, the second port is to be coupled to a fluid source, and a first flow through the first internal channel is in a direction opposite of a second flow through the second internal channel.

5. The handpiece of claim 1 wherein the first distance between the second and third handle portions increases from a first position, where the first and second handle portions are joined, to a second position, proximal to the first position, and
   the first distance between the second and third handle portions decreases from the second position to a third position, proximal to the second position.

6. The handpiece of claim 5 wherein the second handle portion is curved, and the third handle portion is curved.

7. The handpiece of claim 1 wherein a length of a periphery of the first handle portion is greater than the second handle portion.

8. The handpiece of claim 4 wherein the second opening of the tip is positioned closer to a periphery of the tip than the first opening.

9. The handpiece of claim 1 wherein the first handle portion comprises a grip pad for a user's finger, inserted between the second and third handle portions.

10. The handpiece of claim 1 wherein the first, second, and third handle portions comprise polymer material.

11. The handpiece of claim 1 wherein the first, second, and third handle portions comprise tacky coating on a base material.

12. The handpiece of claim 1 wherein the tip is removable and replaceable.

13. The handpiece of claim 1 wherein the first handle portion comprises a larger length of about its periphery than the third handle portion.

14. The handpiece of claim 1 wherein the first distance between the second and third handle portions increases from a first position, where the first and second handle portions are joined, to a second position, proximal to the first position,
   the first distance between the second and third handle portions decreases from the second position to a third position, proximal to the second position,
   a length of a periphery of the first handle portion is greater than the second handle portion, and the length of a periphery of the first handle portion is greater than the third handle portion,
   the first port is to be coupled to a vacuum source, the second port is to be coupled to a fluid source, and a first flow through the first internal channel is in a direction opposite of a second flow through the second internal channel, and
   the second opening of the tip is positioned closer to a periphery of the tip than the first opening.

15. A handpiece for a microdermabrasion system comprising:
   a head base, at a distal end of the handpiece, comprising a first port, a second port, and a cannula located on a top surface of the head base, wherein the first port is located in the cannula, the second port is located in the top surface, and the second port is adjacent to the cannula;

a first portion of a handle of the handpiece couples to the head base;

a second portion of the handle, coupled to the first portion;

a third portion of the handle, coupled to the first and second portions, wherein the second and third portions are separated by a first distance between them;

a third port, coupled to an end of the second portion, wherein the third port couples to a first internal channel passing through the second and first portions of the handle, and the first internal channel couples to the first port of the head base; and a fourth port, coupled to an end of the third portion, wherein the fourth port couples to a second internal channel passing through the third and first portions of the handle, and the second internal channel couples to the second port of the head base, and the first port is separate from the second port at the head base.

16. The handpiece of claim 15 comprising a tip, wherein the tip couples to the head base, the tip comprises a fifth port, and the fifth port of the tip couples to the first port of the head base.

17. The handpiece of claim 16 wherein the tip comprises a first opening and the fifth port couples to the first opening.

18. The handpiece of claim 17 wherein the tip comprises a recess that fits over the cannula and the fifth port of the tip couples to the first port of the cannula in the recess.

19. The handpiece of claim 18 comprising a tip holder, wherein the tip holder comprises an opening, and an inner wall of the opening couples to the tip and a side surface of the head base.

20. The handpiece of claim 19 wherein the top and side surfaces are coupled at a top edge of the head base.

21. The handpiece of claim 19 wherein a first end of the opening of the tip holder couples to the side surface of the head base is larger than a second end of the opening, and the first and second ends of the opening are opposite ends of the opening.

22. The headpiece of claim 19 wherein the head base comprises a groove formed in the side wall of the head base and an O-ring, the O-ring is fitted at least partially in the groove, and the inner wall of the opening of the tip holder couples to the O-ring.

23. The handpiece of claim 19 wherein the second port of the head base is located in the opening of the tip holder, a sixth port is between the tip and the inner wall of the opening of the tip holder, and the second port of the head base couples to the sixth port.

24. The handpiece of claim 23 wherein a second output is between the tip and the inner wall of the opening of the tip holder, the second output couples to the sixth port, and the first and second outputs are separate outputs.

25. The handpiece of claim 16 wherein the tip comprises an abrasive element.

26. The handpiece of claim 15 wherein the head base comprises a lip, wherein the lip forms a portion of the side wall and couples to the top surface of the head base, a top of the lip is higher than the top surface of the head base and lower than a top surface of the cannula.

27. The handpiece of claim 15 wherein a first radius of the lip is greater than a second radius of the top surface.

28. The handpiece of claim 15 wherein the first radius of the lip is greater than a second radius of the cannula.

29. The handpiece of claim 15 wherein the first distance between the second and third handle portions is greater than a width of the first portion of the handle.

30. A handpiece for a microdermabrasion system comprising:

a tip, at a distal end of the handpiece, wherein the tip comprises an abrasive element comprising a first abrasive element channel opening at a proximal end, a second abrasive element channel opening at a distal end, and an abrasive member at the distal end, and a first opening, which is removably coupled to the first abrasive element channel opening;

a second opening, which is not coupled to the first abrasive element channel opening;

a tip holder, wherein the second opening is between is between the tip holder and the abrasive element, the tip holder comprises a third opening and a fourth opening, the fourth opening is larger than the third opening, through the fourth opening the tip holder is placed over the abrasive element, abrasive member, and first opening the tip, and the abrasive member is exposed by the third opening, and an inner surface of the tip holder is coupled against the tip;

a first portion of a handle coupled to the tip;

a second portion of the handle, coupled to the first portion;

a third portion of the handle, coupled to the first and second portions;

a first port, coupled to an end of the second portion, wherein the first port couples to a first internal channel passing through the second and first portions of the handle, the first internal channel is coupled to the first opening at the tip, and a first tubing will be coupled to the first port; and a second port, coupled to an end of the third portion, wherein the second port couples to a second internal channel passing through the third and first portions of the handle, the second internal channel is coupled to the second opening at the tip, and a second tubing will be coupled to the second port, at a first position of the handle, the second and third portions are separated by a first distance that is a greatest distance between the second and third portion, and at a second position of the handle, the end of the second portion and the end of the third portion is separated by a second distance that is less than the first distance.

31. The handpiece of claim 30 wherein the first portion of the handle comprises a concave recess on a first side of the first portion of the handle.

32. The handpiece of claim 31 wherein the first portion of the handle comprises a ridge surrounding the concave recess.

33. The handpiece of claim 30 wherein the first portion of the handle comprises a first flat surface on a second side of the first portion of the handle and a second flat surface on a third side of the first portion of the handle.

34. The handpiece of claim 33 wherein the first and second flat surfaces are not visible from a top view of the concave recess on the first side of the first portion of the handle.

35. The handpiece of claim 30 wherein the first portion of the handle comprises a flat surface on a second side of the first portion of the handle and the first and second sides are opposite sides of the first portion of the handle.

36. The handpiece of claim 30 wherein the second and third portions of the handle are coplanar.

\* \* \* \* \*